US012576139B2

(12) United States Patent
Li

(10) Patent No.: US 12,576,139 B2
(45) Date of Patent: **\*Mar. 17, 2026**

(54) METHOD AND DRUG FOR TREATING SPINAL MUSCULAR ATROPHY

(71) Applicant: Talengen International Limited, Hong Kong (CN)

(72) Inventor: Jinan Li, Beijing (CN)

(73) Assignee: Talengen International Limited, Hong Kong (CN)

( \* ) Notice: Subject to any disclaimer, the term of this patent is extended or adjusted under 35 U.S.C. 154(b) by 568 days.

This patent is subject to a terminal disclaimer.

(21) Appl. No.: 17/924,617

(22) PCT Filed: Nov. 17, 2020

(86) PCT No.: PCT/CN2020/129461
§ 371 (c)(1),
(2) Date: Nov. 10, 2022

(87) PCT Pub. No.: WO2021/227417
PCT Pub. Date: Nov. 18, 2021

(65) Prior Publication Data
US 2023/0181699 A1 Jun. 15, 2023

(30) Foreign Application Priority Data

May 11, 2020 (WO) ................ PCT/CN2020/089631

(51) Int. Cl.
| | |
|---|---|
| *A61P 25/00* | (2006.01) |
| *A61K 9/00* | (2006.01) |
| *A61K 38/48* | (2006.01) |
| *A61P 11/00* | (2006.01) |
| *A61P 21/00* | (2006.01) |
| *A61P 29/00* | (2006.01) |

(52) U.S. Cl.
CPC ............ *A61K 38/48* (2013.01); *A61K 9/0019* (2013.01); *A61K 9/0073* (2013.01); *A61K 38/484* (2013.01); *A61P 11/00* (2018.01); *A61P 21/00* (2018.01); *A61P 25/00* (2018.01); *A61P 29/00* (2018.01); *C12Y 304/21007* (2013.01)

(58) Field of Classification Search
CPC .... A61K 38/48; A61K 9/0019; A61K 9/0073; A61K 38/484; A61K 38/49; A61P 11/00; A61P 21/00; A61P 25/00; A61P 29/00; C12Y 304/21007
See application file for complete search history.

(56) References Cited

U.S. PATENT DOCUMENTS

| | | | |
|---|---|---|---|
| 3,773,919 | A | 11/1973 | Boswell et al. |
| 6,471,960 | B1 | 10/2002 | Anderson |
| 10,709,771 | B2 | 7/2020 | Li |
| 11,090,372 | B2 | 8/2021 | Li |
| 11,207,387 | B2 | 12/2021 | Li |
| 11,389,515 | B2 | 7/2022 | Li |
| 11,400,142 | B2 | 8/2022 | Li |
| 11,478,535 | B2 | 10/2022 | Li |
| 11,547,746 | B2 | 1/2023 | Li |
| 11,642,397 | B2 | 5/2023 | Li |
| 2002/0165147 | A1 | 11/2002 | Yepes et al. |
| 2003/0219431 | A1 | 11/2003 | Petti et al. |
| 2004/0203101 | A1 | 10/2004 | Hastings et al. |
| 2006/0104969 | A1 | 5/2006 | Oray et al. |
| 2007/0203220 | A1 | 8/2007 | Crandall et al. |
| 2011/0078804 | A1 | 3/2011 | Hu et al. |
| 2011/0086894 | A1 | 4/2011 | Bowser |
| 2013/0136727 | A1* | 5/2013 | Hu ........................... C12N 9/22 424/94.6 |
| 2014/0186423 | A1 | 7/2014 | Gelfand |
| 2018/0360930 | A1 | 12/2018 | Li |
| 2018/0369345 | A1 | 12/2018 | Li |
| 2019/0015485 | A1 | 1/2019 | Li |
| 2019/0083586 | A1 | 3/2019 | Li |
| 2019/0328849 | A1 | 10/2019 | Li |
| 2019/0328850 | A1 | 10/2019 | Li |
| 2019/0343931 | A1 | 11/2019 | Li |
| 2019/0351033 | A1 | 11/2019 | Li |
| 2020/0078449 | A1 | 3/2020 | Li |
| 2020/0085920 | A1 | 3/2020 | Li |
| 2021/0154275 | A1 | 5/2021 | Li |
| 2022/0218799 | A1 | 7/2022 | Li |

(Continued)

FOREIGN PATENT DOCUMENTS

| | | |
|---|---|---|
| CN | 1961070 A | 5/2007 |
| CN | 101384256 A | 3/2009 |

(Continued)

OTHER PUBLICATIONS

Aisina, R.B. et al. (Jun. 10, 2011). "Mechanism of the Inhibitory Effect of Angiostatin on Plasminogen Activation by its Physiologic Activators," Russian Journal of Bioorganic Chemistry 37(3):285-291.

Blondet, B. et al. (May 15, 1992). "Plasminogen Activators in The Neuromuscular System of the Wobbler Mutant Mouse," Brain Research I. 580:303-310.

Bruno, M.A. et al. (Apr. 25, 2006). "Activity-Dependent Release of Precursor Nerve Growth Factor, Conversion to Mature Nerve Growth Factor, and its Degradation by a Protease Cascade," PNAS 103(17):6735-6740.

(Continued)

*Primary Examiner* — Sharmila G Landau
*Assistant Examiner* — Ashley T White
(74) *Attorney, Agent, or Firm* — Morrison & Foerster LLP

(57) ABSTRACT

Provided is a method for treating spinal muscular atrophy (SMA), comprising: administrating a therapeutically effective amount of a plasminogen pathway activator to a subject. Further provided are a pharmaceutical composition, product and kit comprising said plasminogen pathway activator, which are used for treating spinal muscular atrophy.

13 Claims, 4 Drawing Sheets

Specification includes a Sequence Listing.

(56) References Cited

U.S. PATENT DOCUMENTS

| | | |
|---|---|---|
| 2023/0066726 A1 | 3/2023 | Li |
| 2023/0081922 A1 | 3/2023 | Li |
| 2023/0084586 A1 | 3/2023 | Li |
| 2023/0139956 A1 | 5/2023 | Li |
| 2023/0141921 A1 | 5/2023 | Li |
| 2023/0143354 A1 | 5/2023 | Li |
| 2023/0173039 A1 | 6/2023 | Li |
| 2023/0190891 A1 | 6/2023 | Li |
| 2023/0302102 A1 | 9/2023 | Li |
| 2023/0346897 A1 | 11/2023 | Li |
| 2024/0000903 A1 | 1/2024 | Li |
| 2024/0000904 A1 | 1/2024 | Li |

FOREIGN PATENT DOCUMENTS

| | | |
|---|---|---|
| CN | 101918548 A | 12/2010 |
| CN | 102154253 A | 8/2011 |
| CN | 108210917 A | 6/2018 |
| CN | 107603951 B | 8/2020 |
| EP | 0058481 B1 | 10/1986 |
| EP | 3967322 A1 | 3/2022 |
| EP | 4140498 A4 | 3/2023 |
| EP | 4249504 A1 | 9/2023 |
| KR | 2010-0049303 A | 5/2010 |
| TW | 201625294 A | 7/2016 |
| TW | 202200192 A | 1/2022 |
| WO | 1994/19461 A1 | 9/1994 |
| WO | 2001/24782 A2 | 4/2001 |
| WO | 2001/24784 A2 | 4/2001 |
| WO | 200125252 A1 | 4/2001 |
| WO | 2001/58476 A2 | 8/2001 |
| WO | 2001/62799 A2 | 8/2001 |
| WO | 2002/32446 A2 | 4/2002 |
| WO | 2002/096356 A2 | 12/2002 |
| WO | 2003/071267 A1 | 8/2003 |
| WO | 2005105990 A2 | 11/2005 |
| WO | 2006/136419 A2 | 12/2006 |
| WO | 2007/026567 A1 | 3/2007 |
| WO | 2007098278 A2 | 8/2007 |
| WO | 2009/036336 A2 | 3/2009 |
| WO | 2009073471 A1 | 6/2009 |
| WO | 2009/146178 A1 | 12/2009 |
| WO | 2010/124185 A1 | 10/2010 |
| WO | 2011/004011 A1 | 1/2011 |
| WO | 2011/062762 A2 | 5/2011 |
| WO | 2012/145428 A2 | 10/2012 |
| WO | 2012151525 A1 | 11/2012 |
| WO | 2014113878 A1 | 7/2014 |
| WO | 2016095013 A1 | 6/2016 |
| WO | 2017/028782 A1 | 2/2017 |
| WO | 2017101867 A1 | 6/2017 |
| WO | 2017101868 A1 | 6/2017 |
| WO | 2017101870 A1 | 6/2017 |
| WO | 2017101871 A1 | 6/2017 |
| WO | 2018107684 A1 | 6/2018 |
| WO | 2018107685 A1 | 6/2018 |
| WO | 2018107688 A1 | 6/2018 |
| WO | 2018107692 A1 | 6/2018 |
| WO | 2018107707 A1 | 6/2018 |
| WO | 2018108161 A1 | 6/2018 |
| WO | 2018/233604 A1 | 12/2018 |
| WO | 2019114839 A1 | 6/2019 |
| WO | 2020/228681 A1 | 11/2020 |
| WO | 2021143906 A1 | 7/2021 |
| WO | 2021155867 A1 | 8/2021 |
| WO | 2021160092 A1 | 8/2021 |
| WO | 2021170099 A1 | 9/2021 |
| WO | 2021190558 A1 | 9/2021 |
| WO | 2021190561 A1 | 9/2021 |
| WO | 2021190562 A1 | 9/2021 |
| WO | 2021190563 A1 | 9/2021 |
| WO | 2021/227417 A1 | 11/2021 |
| WO | 2021228086 A1 | 11/2021 |
| WO | 2022037687 A1 | 2/2022 |
| WO | 2022/105788 A1 | 5/2022 |
| WO | 2022105789 A1 | 5/2022 |

OTHER PUBLICATIONS

Diaz-Ramos, A. et al. (Dec. 11, 2012). "Requirement of Plasminogen Binding to its Cell-Surface Receptor a-Enolase for Efficient Regeneration of Normal and Dystrophic Skeletal Muscle," PLOS One 7(12):e50477, 13 pages.

Extended European Search Report, dated Oct. 5, 2023, for European Patent Application No. 20935975.1, 20 pages.

Henderson, C.E. et al. (Jan. 1, 1988). "Nerve Growth Factors: A Hypothesis on Their Role in the Pathogenesis of Infantile Spinal Amyotrophies," Rev. Neurol. 144(11):730-736. Abstract Only, 1 page.

International Preliminary Report on Patentability, issued Nov. 15, 2022, for PCT/CN2020/129461, filed Nov. 17, 2020, 5 pages.

International Search Report and Written Opinion, mailed Feb. 20, 2021, for PCT/CN2020/129461, filed Nov. 17, 2020, 13 pages. English Translation.

Lorson, C.L et al. (2010, e-pub. Apr. 13, 2010). "Spinal Muscular Atrophy: Mechanisms and Therapeutic Strategies," Human Molecular Genetics 19(1):R111-R118.

Naderi, J. et al. (Aug. 2009). "Plasminogen Activator Inhibitor Type 1 Up-Regulation is Associated with Skeletal Muscle Atrophy and Associated Fibrosis," The American Journal of Pathology 175(2):763-771.

Novokhatny et al. (Jan. 1, 2008, e-pub. Aug. 21, 2008). "Structure and Activity of Plasmin and Other Direct Thrombolytic Agents," Thrombosis Research 122:S3-S8.

SPROULE , D.M. et al. (2010, e-pub. Apr. 30, 2010). "Therapeutic Developments in Spinal Muscular Atrophy," Therapeutic Advances in Neurological Disorders 3(3):1-13.

Srivastava, G. et al. (2019, e-pub. Jul. 4, 2019). "Spinal Muscular Dystrophy—A Revisit of the Diagnosis and Treatment Modalities," International Journal of Neuroscience, pp. 1-17.

Tian, B.-B. et al. (May 15, 2018). "Research Progress of Tissue Plasminogen Activator," Journal of Postgraduate Medical Sciences 31(5):529-534. English Abstract.

U.S. Appl. No. 18/037,299, filed May 16, 2023, Li, Jinan (Copy not submitted herewith pursuant to the waiver of 37 C.F.R. 1.98(a)(2)(iii) issued by the Office on Sep. 21, 2004).

U.S. Appl. No. 18/037,300, filed May 16, 2023, Li, Jinan (Copy not submitted herewith pursuant to the waiver of 37 C.F.R. 1.98(a)(2)(iii) issued by the Office on Sep. 21, 2004).

Wang, T. et al. (Dec. 1, 2021). "Plasminogen is Efficacious in Treating Type II Spinal Muscular Atrophy (SMA)," 19 pages.

Wang, T. et al. (Dec. 1, 2021). "Plasminogen Shows Rapid Efficacy in Treating Patients with Type I Spinal Muscular Atrophy (SMA)," 27 pages.

Zou, T. et al. (Jan. 2006). "Exogenous Tissue Plasminogen Activator Enhances Peripheral Nerve Regeneration and Functional Recovery After Injury In Mice," J. Neuropathol. Exp. Neurol. 65(1):78-86.

Angelucci, F. et al. (Mar. 31, 2019). "Amyloid Beta Soluble Forms and Plasminogen Activation System in Alzheimer's Disease Consequences on Extracellular Maturation of Brain-Derived Neurotrophic Factor and Therapeutic Implications," CNS Neuroscience & Therapeutics 25(3.31):303-313.

Beal, M.F. et al. (2008, e-pub. Mar. 14, 2008). "The Urokinase System of Plasminogen Activator Plays a Role in Amyotrophic Lateral Sclerosis (ALS) Pathogenesis," Experimental Neurology 211(2):332-333.

Demestre, M. et al. (Apr. 2006). "Serine-Proteases Purified from Sear of Patients with Amyotrophic Lateral Sclerosis (ALS) Induce Contrasting Cytopathology in Murine Motoneurones to IgG," Neuropathol App. Neurobiol. 32:141-156, Abstract Only.

Glas, M. et al. (Sep. 22, 2007). "A Role for the Urokinase-Type Plasminogen Activator System in Amyotrophic Lateral Sclerosis," Experimental Neurology 207(2):350-356.

Goldenberg, M.M. et al. (Mar. 2012). "Multiple Sclerosis Review," Pharmacy and Therapeutics 37(3):175-184.

(56) References Cited

OTHER PUBLICATIONS

Gutierrez-Fernandez, A. et al. (May 21, 2007). "Plasminogen Gene Expression in Regulated by Nerve Growth Factor," J. Thromb. Haemost. 5(8):1715-1725.

Iulita, M.F. et al. (Mar. 1, 2014). "Nerve Growth Factor Metabolic Dysfunction in Down's Syndrome Brains," Brain 137(3):860-872.

Iulita, M.F. et al. (Sep. 1, 2017). "Differential Deregulation of NGF and BDNF Neurotrophins in a Transgenic Rat Model of Alzheimer's Disease," Neurobiology of Disease 108:307-323.

Lin, Z et al. (May 13, 2016). "Study on Plasminogen and BDNF Expression in the Hippocampus of Depression Rat Mode and its Relationship," Chongquing Medicine 45(9):1170-1109. English Abstract.

Long, Y. et al. (Nov. 23, 2019). "Influence of Intravenous Thrombolysis with Mouse Nerve Growth Factor for Injection and Recombinant Tissue-Type Plasminogen Activator on Neurological Function of Patients with Acute Cerebral Infarction," Journal of Clinical Medicine in Practice 23:7-10. English Abstract.

Pang, T.P. et al. (Oct. 15, 2004). "Cleavage of proBDNF by tPA/Plasmin is Essential for Long-Term Hippocampal Plasticity," Science 306(5695):487-491.

Pentz, R. et al. (Jun. 2, 2020). "The Human Brain NGF Metabolic Pathway is Impaired in the Pre-Clinical and Clinical Continuum of Alzheimer's Disease," Molecular Psychiatry 26(10):6023-6037, 25 pages.

Pentz, R. et al. (Oct. 30, 2020). "A New Role for Matrix Metalloproteinase-3 in the NGF Metabolic Pathway: Proteolysis of Mature NGF and Sex-Specific Differences in the Continuum of Alzheimer's Pathology," Neurobiology of Disease 148:105150, 12 pages.

Perez-Martin, M.Y. et al. (2017). "Can Fibrinolytic System Components Explain Cognitive Impairment in Multiple Sclerosis?" Journal of the Neurological Sciences 382:66-72.

Sanderson-Smith, M.L. (2012). "Bacterial Plasminogen Receptors: Mediators of a Multifaceted Relationship," Journal of Biomedicine and Biotechnology 2012:272148, 14 pages.

Seeds, N. et al. (2011. e-pub. May 14, 2011). "Plasminogen Activator Promotes Recovery Following Spinal Cord Injury," Cellular and Molecular Neurobiology 31(6):961-967.

Seeds, N.W. et al. (Nov. 30, 2009). "Role of Plasminogen Activator in Spinal Cord Remodeling After Spinal Cord Injury," Respiratory Physiology and Neurobiology 169(2):141-149, 19 pages.

Yepes, M. et al. (Apr. 22, 2021). "Plasminogen Activators in Neurovascular and Neurodegenerative Disorders," Int. J. Mol. Sci. 22:4380, 21 pages.

Ziliotto, N. et al. (Apr. 24, 2019). "Coagulation Pathways in Neurological Diseases Multiple Sclerosis," Frontier in Neurology 10(409):1-21.

* cited by examiner

METHOD AND DRUG FOR TREATING SPINAL MUSCULAR ATROPHY

CROSS-REFERENCE TO RELATED APPLICATIONS

This application is a national stage application under 35 U.S.C. § 371 of International Application No. PCT/CN2020/129461, filed Nov. 17, 2020, which claims priority to International Application No. PCT/CN2020/089631, filed May 11, 2020, the entire contents of each priority application are incorporated herein by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name 794922003100SEQLIST.TXT, date recorded: Nov. 7, 2022, size: 47,729 bytes).

FIELD OF THE DISCLOSURE

The present application relates to a method for treating spinal muscular atrophy (SMA) and related disorders, comprising administering an effective amount of a component of plasminogen pathway activator or its related compound, such as plasminogen to a subject suffering from spinal muscular atrophy (SMA) and related disorders, to repair injured nerves and improve clinical symptoms and signs.

BACKGROUND OF THE DISCLOSURE

Spinal muscular atrophy (SMA) is a disease of muscle weakness and muscle atrophy caused by degeneration of motor neurons in anterior horn of the spinal cord. It belongs to autosomal recessive hereditary disease. The most common form of SMA is caused by mutations in the survival motor neuron (SMN) gene, and infantile SMA is the most severe form of this neurodegenerative disorder. The symptoms include muscle weakness, hypotonia, weak crying, limping or tendency to fall, difficulty in sucking or swallowing, accumulation of secretions in the lungs or throat, difficulty in eating, and susceptibility to respiratory infections. Legs tend to be weaker than arms, and fail to reach developmental markers, such as looking up or sitting up. In general, the earlier the symptoms appear, the shorter the lifespan.

The progression of SMA is directly related to the rate at which motor neuron cells deteriorate and the resulting weakness degree. Infants with severe forms of SMA often die from respiratory disease due to weakness of muscles supporting breathing. Children with milder forms of SMA live longer, but they may need extensive medical support.

SMA is an autosomal recessive hereditary disease. About 95% of SMA is caused by mutation of SMN1 (survival motor neuron 1) gene on chromosome 5, so it is also called 5q SMA. 5q SMA is divided into 5 subtypes according to the age of onset of the patients and the severity of the disease: Type 0 patients: generally more common in the fetus or neonate, the onset in the fetal period is manifested as decreased fetal movement, and the neonate manifests as loss of muscle reflexes, facial paralysis, atrial septal defect and joint contracture, the most serious manifestation is respiratory failure, the life expectancy of sick children is greatly shortened, and most survival time is within 6 months. Type I patients: the infantile type, also known as Werdnig-Hoffman disease, which accounts for 50% of SMA patients, the patients present with hypotonia, poor head control, and diminished or absent tendon reflexes within 6 months after birth; severe hypotonia manifests as "frog legs" when lying down, lack of head control, inability to sit upright, weak intercostal muscles, and relatively small diaphragm muscles; patients often suffer from impaired swallowing function and respiratory failure due to respiratory muscle weakness. In absence of assisted ventilation, 92% of children with type I SMA usually die from respiratory failure before 20 months old. Type II patients: intermediate type, accounting for about 20% of SMA patients, it usually occurs within 6-18 months after birth, patients can sit alone at some stage of development, but cannot walk independently; such patients often suffer from complications such as scoliosis, joint contractures, and ankylosis of the mandibular joint; scoliosis and intercostal muscle weakness often lead to severe lung disease, and the cognitive ability of these children is normal. Type III patients: the juvenile type (also known as Kugelberg-Welander disease), accounts for about 30% of SMA patients, and the disease usually occurs within 18 months to 5 years after birth; the patients can walk with the help of adminicle support; unlike type II SMA, most of these patients do not have complications such as scoliosis and respiratory muscle weakness, and the cognition and life expectancy of this population are generally not affected by the disease. Type IV patients: occurring after adolescence, the exercise capacity of the patients is gradually decreased; and those patients account for approximately 5% of the total number of SMA patients; similar to type III, but with onset in adulthood; it is generally believed that the disease occurs at the age of 30 or later, 4% of the SMAs are not caused by mutations in the SMN1 gene, they are called non-5q SMAs, meaning that their pathogenic gene is not located in the SMN region of chromosome 5. Similar to 5q SMA, children with non-5q SMA also have early symptoms of muscle weakness, but there are some differences, including distal rather than proximal muscle weakness, and earlier distal joint contracture, diaphragm paralysis with earlier respiratory failure and cerebellar degeneration (Verhaart I E C, Robertson A, Wilson I J, Aartsma-Rus A, Cameron S, Jones C C, Cook S F, Lochmüller H. Prevalence, incidence and carrier frequency of 5q-linked spinal muscular atrophy—a literature review. Orphanet J Rare Dis. 2017 Jul. 4; 12(1): 124; Sugarman E A, Nagan N, Zhu H, Akmaev V R, Zhou Z, Rohlfs E M, Flynn K, Hendrickson B C, Scholl T, Sirko-Osadsa D A, Allitto B A. Pan-ethnic carrier screening and prenatal diagnosis for spinal muscular atrophy: clinical laboratory analysis of >72,400 specimens. Eur J Hum Genet. 2012 January; 20(1):27-32).

SMA is caused by inactivating mutations or deletions of the telomere copies of a gene (SMN1) on both chromosomes, resulting in loss of function of the SMN1 gene. The SMN1 protein functions as a cofactor in RNA maturation, and is required for the viability of all eukaryotic cells (Talbot and Tizzano (2017) Gene Ther 24(9):529-533). The SMN2 protein is almost identical to SMN1 except for a single mutation that functions in the splicing of RNA messages. All SMA patients retain a centromeric copy of the gene (SMN2), and the number of copies of the SMN2 gene in SMA patients is generally inversely correlated with disease severity, i.e. patients with less severe SMA have more copies of SMN2. Nonetheless, SMN2 cannot fully compensate for the loss of SMN1 function due to alternative splicing of exon 7 caused by a translationally silent C to T mutation in exon 7. Thus, the majority of transcripts produced by SMN2 lack exon 7

(47 SMN2) and encode SMN proteins that have impaired function and are rapidly degraded to truncated form.

Clinically, SMA is usually diagnosed by clinical symptoms combined with a test for at least one copy of the SMN1 gene. In some cases, other tests such as electromyography (EMG) or muscle biopsy can also aid in the diagnosis when the SMN1 gene test shows no abnormalities. So far, the treatment of SMA has been limited to supportive care, including treatment and care for breathing, nutrition, and rehabilitation, and there are no drugs that can effectively treat the disease.

SUMMARY OF THE DISCLOSURE

The present study found that plasminogen pathway activators such as plasminogen can significantly improve the symptoms of nerve injury in SMA subjects, improve lung function, prolong survival, promote transcription and expression of the SMN gene, and increase the level of SMN protein in brain tissue and muscle tissue, promote the expression of NF-κB protein in brain tissue and muscle tissue, promote the formation of mature NGF in brain tissue, improve lung tissue injury, so as to effectively prevent and treat SMA.

In one aspect, the application relates to a method for treating spinal muscular atrophy (SMA), including Type 0, Type I, Type II, Type III, Type IV and non-5q SMA, comprising administering to a subject with motor neuron disease (e.g., spinal muscular atrophy (SMA)) a therapeutically effective amount of one or more plasminogen pathway activators selected from the group consisting of: a component of plasminogen activation pathway, a compound directly activating plasminogen or indirectly activating plasminogen by activating an upstream component of plasminogen activation pathway, a compound mimicking the activity of plasminogen or plasmin, a compound upregulating the expression of plasminogen or an activator of plasminogen, an analog of plasminogen, an analog of plasmin, an analog of tPA or uPA, and an antagonist of fibrinolysis inhibitor.

In some particular embodiments, for a subject with spinal muscular atrophy (SMA), including type 0, type I, type II, type III, type IV and non-5q SMA, the plasminogen pathway activator has one or more activities selected from the group consisting of: 1. reducing or alleviating the severity of SMA; 2. delaying the onset of SMA; 3. inhibiting the progression of SMA; 4. extending the survival time of the subjects; 5. improving the quality of life of the subjects and/or improving the mental state of the subjects; 6. reducing the number of SMA-related symptoms; 7. reducing or alleviating the severity of one or more symptoms associated with SMA; 8. reducing the duration of symptoms associated with SMA; 9. preventing recurrence of symptoms associated with SMA; 10. inhibiting the development or onset of SMA symptoms; 11. inhibiting the progression of symptoms associated with SMA; 12. improving lung function; 13. improving blood oxygen saturation; 14. promoting the transcription and expression of SMN gene; 15. increasing the level of SMN protein in brain tissue and muscle tissue; 16. promoting the expression of NF-κB protein in brain tissue and muscle tissue; 17. promoting the formation of mature NGF in brain tissue; 18. reducing lung tissue injury; 19. increasing muscle strength; 20. reducing muscle atrophy; 21. reducing motor neuron loss; 22. promoting growth and development; and/or 23. improving motor function. In some particular embodiments, the plasminogen pathway activator alleviates muscle atrophy, increases muscle strength, and/or improves muscle tone in the subjects. In some particular embodiments, the plasminogen pathway activator prolongs survival of the subjects. In some particular embodiments, the plasminogen pathway activator promotes transcription and/or expression of the SMN gene. In some particular embodiments, the plasminogen pathway activator promotes recovery of muscle function in the subjects. In some particular embodiments, the plasminogen pathway activator promotes repair of neuron injury in anterior horn of spinal cord in the subjects. In some particular embodiments, the plasminogen pathway activator promotes the expression of NF-κB protein in the subjects. In some particular embodiments, the plasminogen pathway activator promotes the formation of mature NGF in the subjects. The plasminogen pathway activator promotes the formation of mature NGF in the subjects.

In some embodiments, the plasminogen pathway activator is administered in combination with one or more other medicaments and/or therapies, preferably the therapies include cell therapy (e.g., stem cell therapy) and gene therapy, such as antisense RNA, small molecule splicing modifiers.

In some embodiments, the plasminogen pathway activator is a component of a plasminogen activation pathway.

In some embodiments, the component of the plasminogen activation pathway is selected from the group consisting of: plasminogen, recombinant human plasmin, Lys-plasminogen, Glu-plasminogen, plasmin, a variant of plasminogen and plasmin and the analog thereof comprising one or more kringle domains and protease domains of plasminogen and plasmin, mini-plasminogen, mini-plasmin, micro-plasminogen, micro-plasmin, delta-plasminogen, delta-plasmin, an activator of plasminogen, tPA and uPA. In some particular embodiments, the antagonist of the fibrinolysis inhibitor is an antagonist of PAI-1, complement C1 inhibitor, α2 antiplasmin or α2 macroglobulin, e.g., an antibody of PAI-1, complement C1 inhibitor, α2 anti-plasmin or α2 macroglobulin. In some particular embodiments, the component of the plasminogen activation pathway is plasminogen. In some particular embodiments, the plasminogen comprises or has an amino acid sequence having at least 75%, 80%, 85%, 90%, 95%, 96%, 97%, 98% or 99% sequence identity with the amino acid sequence represented by SEQ ID NO: 2, 6, 8, 10 or 12, and has plasminogen activity. In some embodiments, the plasminogen activity is the proteolytic activity of plasminogen. In some embodiments, the plasminogen activity is the lysine binding activity of plasminogen to a substrate molecule. In some embodiments, the plasminogen activity is the proteolytic activity of plasminogen and the lysine binding activity of plasminogen to a substrate molecule. In some embodiments, the plasminogen is a protein having an amino acid sequence with addition, deletion and/or substitution of 1-100, 1-90, 1-80, 1-70, 1-60, 1-50, 1-45, 1-40, 1-35, 1-30, 1-25, 1-20, 1-15, 1-10, 1-5, 1-4, 1-3, 1-2, or 1 amino acid based on the sequence represented by SEQ ID NO: 2, 6, 8, 10 or 12, and having proteolytic activity and/or lysine binding activity of plasminogen. In some particular embodiments, the plasminogen activity is the proteolytic activity of plasminogen. In some particular embodiments, the plasminogen is a protein comprising a plasminogen active fragment and having the proteolytic activity and/or lysine binding activity of plasminogen. In some embodiments, the plasminogen active fragment comprises or has a serine protease domain of plasminogen or a plasminogen protease domain. In some particular embodiments, the amino acid sequence of the plasminogen active fragment is represented by SEQ ID NO: 14. In some particular embodiments, the plasminogen is selected from the group consisting of: Glu-plasminogen (human full-length plasminogen), Lys-plasminogen (human full-length plasminogen cleaved between amino acids 76-77), small plasminogen (containing Kringle 5 (K5) and serine protease domain), micro-plasminogen (containing serine protease domains), delta-plasminogen (containing Kringle 1 and serine protease domain), or a variant thereof retaining plasminogen activity. In some embodiments, the plasminogen is human full-length plasminogen, or a variant or fragment thereof still retaining plasminogen activity. In some embodiments, the plasminogen activity is the proteolytic activity of plasminogen. In some embodiments, the plasminogen activity is the lysine binding activity of plasminogen to a substrate molecule. In some embodiments, the plasminogen activity is the proteolytic activity of plasminogen and the lysine binding activity of plasminogen to a substrate molecule. In some embodiments, the plasminogen is a human plasminogen ortholog from a primate or rodent, or a variant or fragment thereof still retaining the proteolytic activity and/or lysine binding activity of plasminogen. In some embodiments, the plasminogen comprises the amino acid sequence represented by SEQ ID NO: 2, 6, 8, 10, or 12. In some embodiments, the plasminogen is human native plasminogen.

In some particular embodiments, the plasminogen pathway activator is administered systemically or locally, e.g., by intravenous administration, intramuscular administration, intrathecal administration, nasal inhalation, aerosol inhalation, nasal or eye drops. In some embodiments, the subject is a human. In some embodiments, the subject is lack of or deficient in plasminogen. In some embodiments, the lack or deficiency is congenital, secondary and/or local. In some embodiments, the plasminogen is administered at a dose of 0.0001-2000 mg/kg, 0.001-800 mg/kg, 0.01-600 mg/kg, 0.1-400 mg/kg, 1-200 mg/kg, 1-100 mg/kg, 10-100 mg/kg (calculated by per kilogram of body weight); or at a dose of 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$, 10-100 mg/cm$^2$ (calculated by per square centimeter of body surface area) every day, every two days, or every three days continuously.

In some embodiments, the above-mentioned SMA is a type 0, type I, type II, type III, type IV or non-5q SMA.

In one aspect, the application also relates to a pharmaceutical composition, medicament, preparation, kit, or product for treating spinal muscular atrophy (SMA), comprising the above mentioned plasminogen pathway activator, such as a component of the plasminogen activation pathway (e.g., plasminogen) as described above.

In some embodiments, the pharmaceutical composition, medicament, formulation comprises a pharmaceutically acceptable carrier and a plasminogen pathway activator, e.g., a component of the plasminogen activation pathway described above, such as plasminogen described above. In some embodiments, the kit or product comprises one or more containers containing the pharmaceutical composition, medicament or formulation. In some embodiments, the kit or product further comprises a label or instructions for use indicating the method for using a plasminogen pathway activator, e.g., a component of the plasminogen activation pathway described above, such as a method for treating spinal muscular atrophy with plasminogen described above. In some embodiments, the kit or product further comprises another one or more additional containers containing one or more other medicaments. In some embodiments, the above-mentioned SMA is type 0, type I, type II, type III, type IV or non-5q SMA.

In one aspect the present application also relates to a plasminogen pathway activator as described above, such as plasminogen as described above, for use in the treatment of spinal muscular atrophy (SMA). In some embodiments, the above-mentioned SMA is type 0, type I, type II, type III, type IV or non-5q SMA.

In one aspect, the present application also relates to use of a plasminogen pathway activator as described above, such as plasminogen as described above for treating spinal muscular atrophy (SMA). In some embodiments, the above-mentioned SMA is type 0, type I, type II, type III, type IV or non-5q SMA.

In one aspect, the present application also relates to use of a therapeutically effective amount of the above plasminogen pathway activator (e.g., a component of the plasminogen activation pathway described above, such as the plasminogen described above) in the preparation of a pharmaceutical composition, medicament, preparation, kit, or product for treating spinal muscular atrophy (SMA).

In some embodiments, the plasminogen pathway activator is selected from one or more of the following: a component of plasminogen activation pathway, a compound directly activating plasminogen or indirectly activating plasminogen by activating an upstream component of plasminogen activation pathway, a compound mimicking the activity of plasminogen or plasmin, a compound upregulating the expression of plasminogen or an activator of plasminogen, an analog of plasminogen, an analog of plasmin, an analog of tPA or uPA, and an antagonist of fibrinolysis inhibitor.

In some particular embodiments, the component of plasminogen activation pathway is selected from the group consisting of: plasminogen, recombinant human plasmin, Lys-plasminogen, Glu-plasminogen, plasmin, a variant of plasminogen and plasmin and the analog thereof comprising one or more kringle domains and protease domains of plasminogen and plasmin, mini-plasminogen, mini-plasmin, micro-plasminogen, micro-plasmin, delta-plasminogen, delta-plasmin, an activator of plasminogen, tPA and uPA. In some particular embodiments, the antagonist of the fibrinolysis inhibitor is an antagonist of PAI-1, complement C1 inhibitor, α2 antiplasmin, or α2 macroglobulin, e.g., an antibody of PAI-1, complement C1 inhibitor, α2 anti-plasmin, or α2 macroglobulin.

In some embodiments, the plasminogen pathway activator is a component of a plasminogen activation pathway.

In some embodiments, the components of the plasminogen activation pathway are selected from the group consisting of: plasminogen, recombinant human plasmin, Lys-plasminogen, Glu-plasminogen, plasmin, a variant of plasminogen and plasmin and the analog thereof comprising one or more kringle domains and protease domains of plasminogen and plasmin, mini-plasminogen, mini-plasmin, micro-plasminogen, micro-plasmin, delta-plasminogen, delta-plasmin, plasminogen activator, tPA and uPA. In some particular embodiments, the antagonist of the fibrinolysis inhibitor is an antagonist of PAI-1, complement C1 inhibitor, α2 antiplasmin, or α2 macroglobulin, e.g., an antibody of PAI-1, complement C1 inhibitor, α2 anti-plasmin, or α2 macroglobulin.

In some particular embodiments, the component of the plasminogen activation pathway is plasminogen. In some particular embodiments, the plasminogen comprises or has an amino acid sequence having at least 75%, 80%, 85%, 90%, 95%, 96%, 97%, 98% or 99% sequence identity with the amino acid sequence represented by SEQ ID NO: 2, 6, 8, 10 or 12, and has plasminogen activity. In some embodiments, the plasminogen activity is the proteolytic activity of plasminogen. In some embodiments, the plasminogen activity is the lysine binding activity of plasminogen to a substrate molecule. In some embodiments, the plasminogen activity is the proteolytic activity of plasminogen and the lysine binding activity of plasminogen to a substrate molecule. In some embodiments, the plasminogen is a protein having an amino acid sequence with addition, deletion and/or substitution of 1-100, 1-90, 1-80, 1-70, 1-60, 1-50, 1-45, 1-40, 1-35, 1-30, 1-25, 1-20, 1-15, 1-10, 1-5, 1-4, 1-3, 1-2, or 1 amino acid based on the sequence represented by SEQ ID NO: 2, 6, 8, 10 or 12, and having proteolytic activity and/or lysine binding activity of plasminogen. In some particular embodiments, the plasminogen activity is the proteolytic activity of plasminogen. In some particular embodiments, the plasminogen is a protein comprising a plasminogen active fragment and having the proteolytic activity and/or lysine binding activity of plasminogen. In some embodiments, the plasminogen active fragment comprises or has a serine protease domain of plasminogen or a plasminogen protease domain. In some particular embodiments, the amino acid sequence of the plasminogen active fragment is represented by SEQ ID NO: 14. In some particular embodiments, the plasminogen is selected from the group consisting of: Glu-plasminogen (human full-length plasminogen), Lys-plasminogen (human full-length plasminogen cleaved between amino acids 76-77), small plasminogen (containing Kringle 5 (K5) and serine protease domain), micro-plasminogen (containing serine protease domains), delta-plasminogen (containing Kringle 1 and serine protease domain), or a variant thereof retaining plasminogen activity. In some embodiments, the plasminogen is human full-length plasminogen, or a variant or fragment thereof still retaining plasminogen activity. In some embodiments, the plasminogen activity is the proteolytic activity of plasminogen. In some embodiments, the plasminogen activity is the lysine binding activity of plasminogen to a substrate molecule. In some embodiments, the plasminogen activity is the proteolytic activity of plasminogen and the lysine binding activity of plasminogen to a substrate molecule. In some embodiments, the plasminogen is a human plasminogen ortholog from a primate or rodent, or a variant or fragment thereof still retaining the proteolytic activity and/or lysine binding activity of plasminogen. In some embodiments, the plasminogen comprises the amino acid sequence represented by SEQ ID NO: 2, 6, 8, 10, or 12. In some embodiments, the plasminogen is human native plasminogen.

In some embodiments, the plasminogen pathway activator, e.g., a component of the plasminogen activation pathway described above, such as plasminogen described above, is administered in combination with one or more other medicaments and/or therapies. In some embodiments, the plasminogen pathway activator, e.g., a component of the plasminogen activating pathway, such as plasminogen, is administered by intravenous administration, intramuscular administration, intrathecal administration, nasal inhalation, aerosol inhalation, nasal or eye drops.

In some embodiments, the pharmaceutical composition, medicament, formulation comprises a pharmaceutically acceptable carrier and a plasminogen pathway activator, e.g., a component of the plasminogen activating pathway, such as plasminogen. In some embodiments, the kit or product comprises one or more containers containing the pharmaceutical composition, medicament or formulation. In some embodiments, the kit or product further comprises a label or instructions for use indicating the method for using a plasminogen pathway activator, e.g., a component of the plasminogen activation pathway, such as plasminogen to treat spinal muscular atrophy.

In some embodiments, the kit or product further comprises one or more additional containers containing one or more other medicaments.

In some embodiments, the above-mentioned SMA is type 0, type I, type II, type III, type IV or non-5q SMA.

The present application explicitly encompasses all the combinations of the technical features belonging to the embodiments of the present application, and these combined technical solutions have been explicitly disclosed in this application, just as the separately and explicitly disclosed above technical solutions. In addition, the present application also explicitly encompasses the combinations of each embodiment and its elements, and the combined technical solutions are explicitly disclosed herein.

BRIEF DESCRIPTION OF THE DRAWINGS

FIG. 4A is the statistical result of the survival curve, and FIG. 4B is the statistical result of the survival time. The statistical results of survival curve show that plasminogen significantly improves the survival curve of SMNΔ7 SMA mice, and the difference is statistically significant (P=0.029). The statistical results of survival time show that the median survival time of the mice in the vehicle group is 14 days, and all mice died on day 15; the median survival time of the plasminogen group is 16 days, and all the mice died on day 17, and the difference in statistical analysis is significant (P=0.03), indicating that plasminogen can prolong the survival time of SMA model mice.

9 in the blank control group, and the level of SMN gene transcription in the mice in the plasminogen group is significantly higher than that in the mice in the vehicle group or the blank control group. The results suggest that plasminogen can promote SMN gene transcription.

Figure 6:
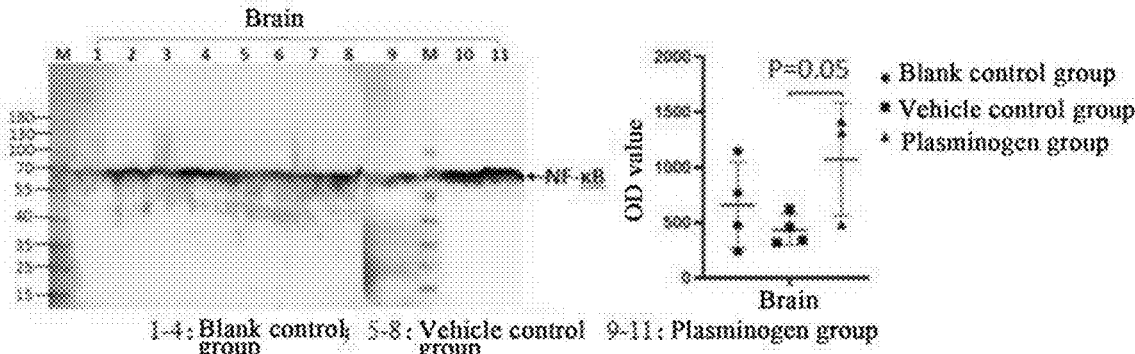

FIG. 6 shows the results of Western blot detection and optical density quantitative analysis of brain NF-κB protein in SMNΔ7 SMA mice after administration of plasminogen. The results show that, the brains of the mice in the blank control group have a certain amount of NF-κB protein, the level of NF-κB protein in the brains of the mice in the vehicle group is lower than that of the mice in the blank control group, and the level of NF-κB protein in the brains of the mice in the plasminogen group is significantly higher than that of the mice in the vehicle group, and the statistical difference is close to significant (P=0.05). These results suggest that plasminogen can promote the increase of NF-κB protein level in brain tissue of SMNΔ7 SMA mice.

Figure 7:
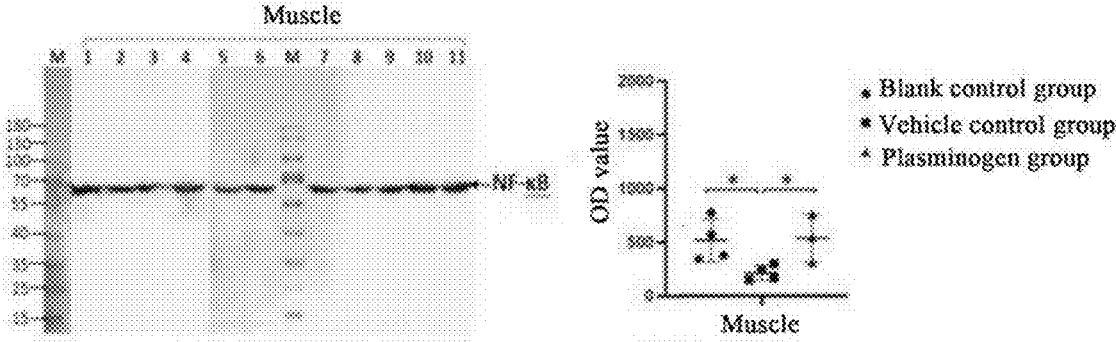

FIG. 7 shows the results of Western blot detection and quantitative optical density analysis of NF-κB protein in representative hindlimb muscles of SMNΔ7 SMA mice after administration of plasminogen. The results show that, the muscles of the mice in the blank control group have a certain amount of NF-κB protein, the level of NF-κB protein in the muscles of the mice in the vehicle group is lower than that of the mice in the blank control group, and the level of NF-κB protein in the muscles of the mice in the plasminogen group is significantly higher than that of the mice in the vehicle group, and the difference is statistically significant (* means P<0.05). These results suggest that plasminogen can promote the increase of muscle NF-κB protein level in SMNΔ7 SMA mice.

Figure 8:
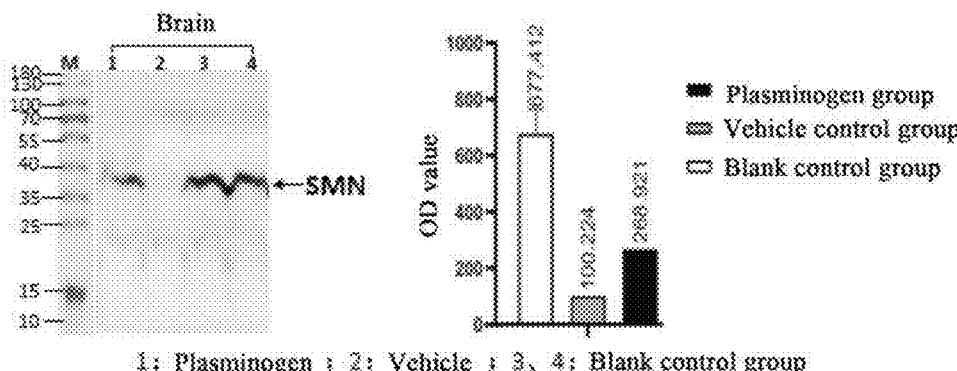

FIG. 8 shows the results of Western blot detection and optical density (OD) quantitative analysis of representative brain SMN protein of SMNΔ7 SMA mice after administration of plasminogen. The results show that, the brains of the mice in the blank control group express a certain amount of SMN protein, the expression level of SMN protein in the mice in the vehicle group is lower than that in the mice in the blank control group, and the expression level of SMN protein in the mice in the plasminogen group is significantly higher than that in the mice in the vehicle group. These results suggest that plasminogen can promote the expression of SMN protein in the brain of SMNΔ7 SMA mice.

Figure 9:
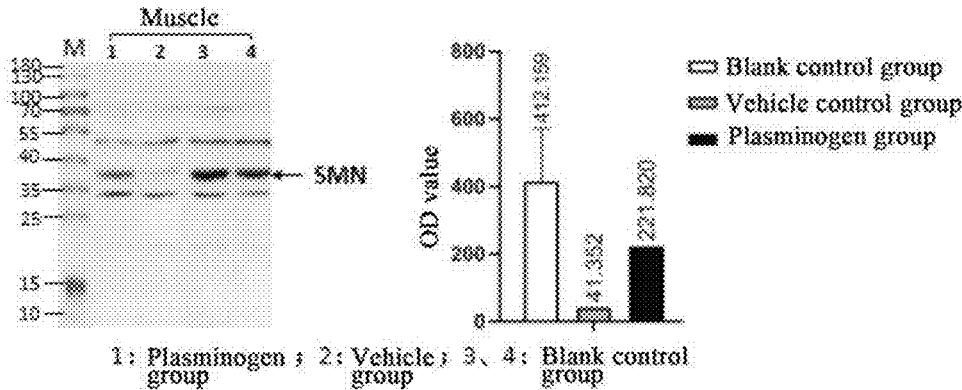

FIG. 9 shows the results of Western blot detection and optical density (OD) quantitative analysis of SMN protein of representative hindlimb muscles of SMNΔ7 SMA mice after administration of plasminogen. The results show that, the muscles of the mice in the blank control group express a certain amount of SMN protein, the expression level of SMN protein in the muscles of the mice in the vehicle group is lower than that of the mice in the blank control group, and the expression level of SMN protein in the muscles of the mice in the plasminogen group is significantly higher than that of the mice in the vehicle group. These results suggest that plasminogen can promote the expression of SMN protein in muscle of SMNΔ7 SMA mice.

Figure 10:
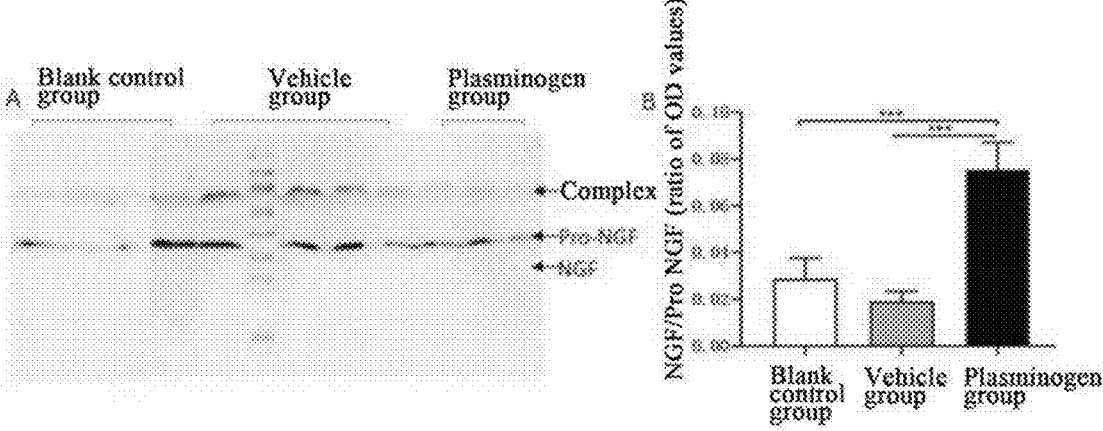

FIG. 10 shows the results of Western blot detection and NGF/Pro-NGF optical density (OD) ratio quantitative analysis of hindbrain tissues of SMA mice after administration of plasminogen. The results show that, the brain tissues of the mice in the blank control group have a certain ratio of NGF/ProNGF, and the ratio of NGF/ProNGF in the brain tissues of the mice in the plasminogen group is significantly higher than that of the mice in the vehicle group, and the statistical difference is extremely significant (*** indicates P<0.001), indicating that plasminogen can promote the transformation of ProNGF into NGF in the brain tissues of SMA model mice, and promote the formation of mature NGF.

Figure 11:
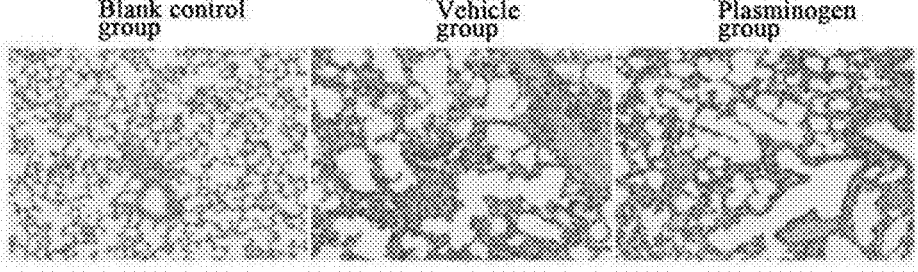

FIG. 11 shows the results of H&E staining of representative posterior lung tissues of SMA mice after administration of plasminogen. The results show that, the terminal bronchiolar epithelial cells of the lung tissue of the mice in the blank control group are neatly arranged and clearly distinguishable; the alveolar cavities are uniform in size, the alveolar space is not thickened, and there is no inflammatory cell infiltration around the blood vessels; as for the lung tissue of the mice in the vehicle group, the respiratory bronchiolar epithelium is fallen off, the alveolar ducts and alveolar sacs are enlarged, the alveolar septum is widened, the alveoli collapse to structural disorder, and there are eosinophils, foam cells, and lymphocytes around the pulmonary blood vessels; the respiratory bronchiolar epithelium of the mice in the plasminogen group are arranged in an orderly manner, the alveolar ducts and alveolar sacs are enlarged, and the alveolar cavities are evenly enlarged, but the alveolar wall composed of a single layer of alveolar epithelium is visible, indicating that plasminogen can alleviate lung tissue injury in SMA model mice.

DETAILED DESCRIPTION

The term "spinal muscular atrophy" (SMA) refers to a disease caused by inactivating mutations or deletions of the SMN1 gene on both chromosomes, resulting in loss of function of the SMN1 gene. Symptoms of SMA include muscle weakness, hypotonia, weak crying, weak coughing, limping or tendency to fall, difficulty in sucking or swallowing, difficulty in breathing, accumulation of secretions in the lungs or throat, clenched fists and sweaty hands, tongue fluttering/vibration, head often tilted to one side (even when lying down), legs tending to be weaker than arms, legs often in "frog legs" position, difficulty in feeding, increased susceptibility to respiratory infections, bowel/bladder weakness, below normal weight, inability to sit without support, inability to walk, inability to crawl, and hypotonia, loss of reflexes, and multiple congenital contractures (joint contractures) associated with loss of anterior horn cells.

The term "treating spinal muscular atrophy (SMA)" or "treatment of spinal muscular atrophy (SMA)" herein includes obtaining one or more of the following effects: 1. reducing or alleviating the severity of SMA; 2. delaying the onset of SMA; 3. inhibiting the progression of SMA; 4. extending the survival time of the subject; 5. improving the quality of life of the subject and/or improving the mental state of the subject; 6. reduce the number of SMA-related symptoms; 7. reducing or alleviating the severity of one or more symptoms associated with SMA; 8. reducing the duration of symptoms associated with SMA; 9. preventing recurrence of symptoms associated with SMA; 10. inhibiting the development or onset of SMA symptoms; 11. inhibiting the progression of symptoms associated with SMA; 12. improving lung function; 13. improving blood oxygen saturation; 14. promoting the transcription and expression of SMN gene; 15. increasing the level of SMN protein in brain tissue and muscle tissue; 16. promoting the expression of NF-κB protein in brain tissue and muscle tissue; 17. promoting the formation of mature NGF in brain tissue; 18. reducing lung tissue injury; 19. increasing muscle strength; 20. reducing muscle atrophy; 21. reducing motor neuron loss; 22. promoting growth and development; and/or 23. improving motor function.

In some embodiments, a component of the plasminogen activation pathway of the present application or a related compound thereof, such as plasminogen described above, enhances SMN gene transcription and/or expression. In some embodiments, a component of the plasminogen activation pathway of the present application, or a related compound thereof, such as the plasminogen described above, increases the expression of SMN protein in a human subject in need thereof.

In some embodiments, a component of the plasminogen activation pathway of the present application or a related compound thereof, such as plasminogen, may be used alone or in combination with other medicaments to treat or prevent diseases caused by inactivating mutations or deletions in the SMN gene or diseases associated with loss or deficiency of SMN gene function. These diseases include, but are not limited to, spinal muscular atrophy (SMA).

In some embodiments, the present application relates to a method for treating a disease, such as SMA, caused by an inactivating mutation or deletion of SMN gene and/or associated with a loss or deficiency of SMN gene function, comprising administering to a subject a therapeutically effective amount of a component of the plasminogen activation pathway or a related compound, such as plasminogen. In some embodiments, the present application relates to a method for treating SMA, comprising administering to a subject a therapeutically effective amount of plasminogen.

In some embodiments, the present application relates to a method for treating SMA, comprising administering to a subject a therapeutically effective amount of plasminogen, wherein the plasminogen has one or more activities selected from the group consisting of: 1. reducing or alleviating the severity of SMA; 2. delaying the onset of SMA; 3. inhibiting the progression of SMA; 4. extending the survival time of the subject; 5. improving the quality of life of the subject and/or improving the mental state of the subject; 6. reducing the number of SMA-related symptoms; 7. reducing or alleviating the severity of one or more symptoms associated with SMA; 8. reducing the duration of symptoms associated with SMA; 9. preventing recurrence of symptoms associated with SMA; 10. inhibiting the development or onset of SMA symptoms; 11. inhibiting the progression of symptoms associated with SMA; 12. improving lung function; 13. improving blood oxygen saturation; 14. promoting the transcription and expression of SMN gene; 15. increasing the level of SMN protein in brain tissue and muscle tissue; 16. promoting the expression of NF-κB protein in brain tissue and muscle tissue; 17. promoting the formation of mature NGF in brain tissue; 18. reducing lung tissue injury; 19. increasing muscle strength; 20. reducing muscle atrophy; 21. reducing motor neuron loss; 22. promoting growth and development; and/or 23. improving motor function.

Fibrinolytic system is a system consisting of a series of chemical substances involved in the process of fibrinolysis, mainly including plasminogen, plasmin, plasminogen activator, and fibrinolysis inhibitor. Plasminogen activators include tissue-type plasminogen activator (t-PA) and urokinase-type plasminogen activator (u-PA). t-PA is a serine protease that is synthesized by vascular endothelial cells. t-PA activates plasminogen, which is mainly carried out on fibrin; urokinase-type plasminogen activator (u-PA) is produced by renal tubular epithelial cells and vascular endothelial cells, and may directly activate plasminogen without the need for fibrin as a cofactor. Plasminogen (PLG) is synthesized by liver. When blood coagulates, a large amount of PLG is adsorbed on the fibrin network, and under the action of t-PA or u-PA it is activated into plasmin to promote fibrinolysis. Plasmin (PL) is a serine protease whose functions are as follows: degrading fibrin and fibrinogen; hydrolyzing various coagulation factors V, VIII, X, VII, XI, and II, etc.; converting plasminogen into plasmin; hydrolyzing complement, etc. Fibrinolysis inhibitors: including plasminogen activator inhibitor (PAI) and α2 antiplasmin (α2-AP). PAI mainly has two forms, PAI-1 and PAI-2, which may specifically bind to t-PA in a ratio of 1:1, thereby inactivating it and activating PLG at the same time. α2-AP is synthesized by liver, and binds to PL in a ratio of 1:1 to form a complex to inhibit the activity of PL; FXIII makes α2-AP covalently bound to fibrin, reducing the sensitivity of fibrin to PL. Substances that inhibit the activity of the fibrinolytic system in vivo: PAI-1, complement C1 inhibitor; α2 antiplasmin; α2 macroglobulin.

The term "plasminogen pathway activator" of the present application encompasses components of the plasminogen activation pathway, compounds capable of directly activating plasminogen or indirectly activating plasminogen by activating upstream components of the plasminogen activation pathway, compounds mimicking the activity of plasminogen or plasmin, compounds up-regulating the expression of plasminogen or plasminogen activator, plasminogen analogs, plasmin analogs, tPA or uPA analogs and antagonists of fibrinolysis inhibitors.

The term "component of the plasminogen activation pathway" according to the present application encompasses:
1. plasminogen, Lys-plasminogen, Glu-plasminogen, micro-plasminogen, delta-plasminogen; variants or analogs thereof;
2. plasmin and a variant or an analog thereof; and
3. plasminogen activators, such as tPA and uPA, and tPA or uPA variants and analogs comprising one or more domains of tPA or uPA, such as one or more kringle domains and proteolytic domains.

The term "antagonist of fibrinolysis inhibitor" encompasses antagonists of PAI-1, complement C1 inhibitor, α2 antiplasmin or α2 macroglobulin, such as an antibody of PAI-1, complement C1 inhibitor, α2 antiplasmin or α2 macroglobulin.

"Variants" of the above plasminogen, plasmin, tPA and uPA include all naturally occurring human genetic variants as well as other mammalian forms of these proteins, as well as a protein obtained by addition, deletion and/or substitution of such as 1-100, 1-90, 1-80, 1-70, 1-60, 1-50, 1-45, 1-40, 1-35, 1-30, 1-25, 1-20, 1-15, 1-10, 1-5, 1-4, 1-3, 1-2, or 1 amino acid, and still retaining the activity of plasminogen, plasmin, tPA or uPA. For example, "variants" of plasminogen, plasmin, tPA and uPA include mutational variants of these proteins obtained by substitution of such as 1-100, 1-90, 1-80, 1-70, 1-60, 1-50, 1-45, 1-40, 1-35, 1-30, 1-25, 1-20, 1-15, 1-10, 1-5, 1-4, 1-3, 1-2, or 1 conservative amino acid.

A "plasminogen variant" of the application encompasses a protein comprising or having at least 75%, 80%, 85%, 90%, 95%, 96%, 97%, 98% or 99% sequence identity with an amino acid sequence of SEQ ID NO: 2, 6, 8, 10 or 12, and retaining the proteolytic and/or lysine-binding activity of plasminogen. For example, a "plasminogen variant" according to the present application may be a protein obtained by addition, deletion and/or substitution of 1-100, 1-90, 1-80, 1-70, 1-60, 1-50, 1-45, 1-40, 1-35, 1-30, 1-25, 1-20, 1-15, 1-10, 1-5, 1-4, 1-3, 1-2, or 1 amino acid on the basis of SEQ ID NO: 2, 6, 8, 10 or 12, and still retaining the proteolytic and/or lysine-binding activity of plasminogen. Particularly, the plasminogen variants according to the present application include all naturally occurring human genetic variants as well as other mammalian forms of these proteins, as well as mutational variants of these proteins obtained by substitution of such as 1-100, 1-90, 1-80, 1-70, 1-60, 1-50, 1-45, 1-40, 1-35, 1-30, 1-25, 1-20, 1-15, 1-10, 1-5, 1-4, 1-3, 1-2, or 1 conservative amino acid.

The plasminogen according to the present application may be a human plasminogen ortholog from a primate or rodent, or a variant thereof still retaining the proteolytic and/or lysine-binding activity of plasminogen, for example, a plasminogen represented by SEQ ID NO: 2, 6, 8, 10 or 12, such as a human natural plasminogen represented by SEQ ID NO: 2.

The "analogs" of the above plasminogen, plasmin, tPA, and uPA include compounds that respectively provide substantially similar effect to plasminogen, plasmin, tPA, or uPA.

The "variants" and "analogs" of above plasminogen, plasmin, tPA and uPA encompass "variants" and "analogs" of plasminogen, plasmin, tPA and uPA comprising one or more domains (e.g., one or more kringle domains and proteolytic domains). For example, "variants" and "analogs" of plasminogen encompass "variants" and "analogs" of plasminogen comprising one or more plasminogen domains (e.g., one or more kringle (K) domains and proteolytic domains, or referred to as serine protease domain, or plasminogen protease domain), such as mini-plasminogen. "Variants" and "analogs" of plasmin encompass "variants" and "analogs" of plasmin comprising one or more plasmin domains (e.g., one or more kringle domains and proteolytic domains), such as mini-plasmin, and delta-plasmin.

Whether a "variant" or "analog" of the above plasminogen, plasmin, tPA or uPA respectively has the activity of plasminogen, plasmin, tPA or uPA, or whether the "variant" or "analog" provides substantially similar effect to plasminogen, plasmin, tPA or uPA, may be detected by methods known in the art, for example, it is measured by the level of activated plasmin activity based on enzymography, ELISA (enzyme-linked immunosorbent assay), and FACS (fluorescence-activated cell sorting method), for example, it is detected by referring to a method selected from the following documents: Ny, A., Leonardsson, G., Hagglund, A. C, Hagglof, P., Ploplis, V. A., Carmeliet, P. and Ny, T. (1999). Ovulation in plasminogen-deficient mice. Endocrinology 140, 5030-5035; Silverstein R L, Leung L L, Harpel P C, Nachman R L (November 1984). "Complex formation of platelet thrombospondin with plasminogen. Modulation of activation by tissue activator". J. Clin. Invest. 74(5):1625-33; Gravanis I, Tsirka S E (February 2008). "Tissue-type plasminogen activator as a therapeutic target in stroke". Expert Opinion on Therapeutic Targets. 12(2):159-70; Geiger M, Huber K, Wojta J, Stingl L, Espana F, Griffin J H, Binder B R (August 1989). "Complex formation between urokinase and plasma protein C inhibitor in vitro and in vivo". Blood. 74(2):722-8.

In some embodiments of the present application, the "component of plasminogen activation pathway" according to the present application is a plasminogen selected from the group consisting of: Glu-plasminogen, Lys-plasminogen, mini-plasminogen, micro-plasminogen, delta-plasminogen, or variants thereof retaining plasminogen activity. In some embodiments, the plasminogen is natural or synthetic human plasminogen, or a conservative mutant variant or fragment thereof still retaining plasminogen activity and/or lysine binding activity. In some embodiments, the plasminogen is a human plasminogen ortholog from a primate or rodent or a conservative mutant variant or fragment thereof still retaining plasminogen activity and/or lysine binding activity. In some embodiments, the amino acid sequence of the plasminogen comprises or has an amino acid sequence represented by SEQ ID NO: 2, 6, 8, 10 or 12. In some embodiments, the plasminogen is a human full length plasminogen. In some embodiments, the plasminogen is a human full length plasminogen represented by SEQ ID NO: 2.

"A compound capable of directly activating plasminogen, or indirectly activating plasminogen by activating an upstream component of plasminogen activation pathway", refers to any compound capable of directly activating plasminogen, or indirectly activating plasminogen by activating an upstream component of plasminogen activation pathway, such as tPA, uPA, streptokinase, saruplase, alteplase, reteplase, tenecteplase, anistreplase, monteplase, lanoteplase, pamiteplase, staphylokinase.

The "antagonist of a fibrinolysis inhibitor" according to the present application is a compound that antagonizes, weakens, blocks, or prevents the action of a fibrinolysis inhibitor. Such fibrinolysis inhibitors are e.g., PAI-1, complement C1 inhibitor, α2 antiplasmin, and α2 macroglobulin. Such an antagonist is: e.g., an antibody of PAI-1, complement C1 inhibitor, α2 antiplasmin, or α2 macroglobulin; or an antisense RNA or small RNA blocking or downregulating the expression of such as PAI-1, complement C1 inhibitor, α2 antiplasmin or α2 macroglobulin; or a compound occupying the binding site of PAI-1, complement C1 inhibitor, α2 antiplasmin, or α2 macroglobulin but without the function of PAI-1, complement C1 inhibitor, α2 antiplasmin, or α2 macroglobulin; or a compound blocking the binding domains and/or active domains of PAI-1, complement C1 inhibitor, α2 antiplasmin, or α2 macroglobulin.

Plasmin is a key component of the plasminogen activation system (PA system). It is a broad-spectrum protease capable of hydrolyzing several components of the extracellular matrix (ECM), including fibrin, gelatin, fibronectin, laminin, and proteoglycans. In addition, plasmin may activate some metalloproteinase precursors (pro-MMPs) to form active metalloproteinases (MMPs). Therefore, plasmin is considered to be an important upstream regulator of extracellular proteolysis. Plasmin is formed by proteolysis of plasminogen by two physiological PAs: tissue-type plasminogen activator (tPA) or urokinase-type plasminogen activator (uPA). Due to the relatively high levels of plasminogen in plasma and other body fluids, it has traditionally been thought that the regulation of the PA system is mainly achieved through the synthesis and activity levels of PAs. The synthesis of components of the PA system is strictly regulated by different factors, such as hormone, growth factor and cytokine. In addition, there are specific physiological inhibitors of plasmin and PAs. The main inhibitor of plasmin is α2-antiplasmin. The activity of PAs is inhibited by plasminogen activator inhibitor-1 (PAI-1) of both uPA and tPA, and regulated by plasminogen activator inhibitor-2 (PAI-2) which mainly inhibits uPA. Certain cell surfaces have uPA-specific cell surface receptors (uPARs) with direct hydrolytic activity.

Plasminogen is a single-chain glycoprotein consisting of 791 amino acids with a molecular weight of approximately 92 kDa. Plasminogen is mainly synthesized in liver, and is abundantly present in the extracellular fluid. The content of plasminogen in plasma is approximately 2 μM. Plasminogen is thus a huge potential source of proteolytic activity in tissues and body fluids. Plasminogen exists in two molecular forms: glutamate-plasminogen (Glu-plasminogen) and lysine-plasminogen (Lys-plasminogen). The naturally secreted and uncleaved form of plasminogen has an amino-terminal (N-terminal) glutamate, and is therefore referred to as glutamate-plasminogen. However, in the presence of plasmin, glutamate-plasminogen is hydrolyzed at Lys76-Lys77 into lysine-plasminogen. Compared with glutamate-plasminogen, lysine-plasminogen has a higher affinity for fibrin, and may be activated by PAs at a higher rate. The Arg560-Val561 peptide bond of these two forms of plasminogen may be cleaved by either uPA or tPA, resulting in the formation of a two-chain protease plasmin linked by disulfide. The amino-terminal part of plasminogen comprises five homologous tri-cycles, i.e., so-called kringles, and the carboxy-terminal part comprises the protease domain. Some kringles comprise lysine-binding sites that mediate the specific interaction of plasminogen with fibrin and its inhibitor $\alpha$2-AP. A recently found plasminogen is a 38 kDa fragment, including kringles1-4, and it is a potent inhibitor of angiogenesis. This fragment is named as angiostatin, and is produced by the hydrolysis of plasminogen by several proteases.

The main substrate of plasmin is fibrin, and the dissolution of fibrin is the key to preventing pathological thrombosis. Plasmin also has substrate specificity for several components of the ECM, including laminin, fibronectin, proteoglycans, and gelatin, indicating that plasmin also plays an important role in ECM remodeling. Indirectly, plasmin may also degrade other components of the ECM, including MMP-1, MMP-2, MMP-3 and MMP-9, by converting certain protease precursors into active proteases. Therefore, it has been proposed that plasmin may be an important upstream regulator of extracellular proteolysis. In addition, plasmin has the ability to activate certain latent forms of growth factors. In vitro, plasmin also hydrolyzes components of the complement system, and releases chemotactic complement fragments.

"Plasmin" is a very important enzyme present in blood that hydrolyzes fibrin clots into fibrin degradation products and D-dimers.

"Plasminogen" is the zymogen form of plasmin According to the sequence in swiss prot, it consists of 810 amino acids calculated by the natural human plasminogen amino acid sequence (SEQ ID NO: 4) containing the signal peptide, and the molecular weight is about 90 kD, and it is a glycoprotein mainly synthesized in liver and capable of circulating in blood, the cDNA sequence encoding this amino acid sequence is represented by SEQ ID NO: 3. Full-length plasminogen contains seven domains: a C-terminal serine protease domain, an N-terminal Pan Apple (PAp) domain, and five Kringle domains (Kringle1-5). Referring to the sequence in swiss prot, its signal peptide comprises residues Met1-Gly19, PAp comprises residues Glu20-Val98, Kringle1 comprises residues Cys103-Cys181, Kringle2 comprises residues Glu184-Cys262, Kringle3 comprises residues Cys275-Cys352, Kringle4 comprises residues Cys377-Cys454, and Kringle5 comprises residues Cys481-Cys560. According to NCBI data, the serine protease domain comprises residues Val581-Arg804.

Glu-plasminogen is a natural full-length plasminogen, consisting of 791 amino acids (without a signal peptide of 19 amino acids); the cDNA sequence encoding this amino acid sequence is represented by SEQ ID NO: 1, and the amino acid sequence is represented by SEQ ID NO: 2. In vivo, there is also a Lys-plasminogen produced by the hydrolysis of the peptide bond between amino acids 76 and 77 of Glu-plasminogen, as represented by SEQ ID NO: 6; and the cDNA sequence encoding this amino acid sequence is represented by SEQ ID NO: 5. Delta-plasminogen ($\delta$-plasminogen) is a fragment of full-length plasminogen that lacks the Kringle2-Kringle5 structure, and only contains Kringle1 and a serine protease domain (also known as a proteolytic domain, or plasminogen protease domain). The amino acid sequence of delta-plasminogen (SEQ ID NO: 8) is reported in a literature, and the cDNA sequence encoding this amino acid sequence is represented by SEQ ID NO: 7. Mini-plasminogen consists of Kringle5 and a serine protease domain, and it is reported that it comprises residues Val443-Asn791 (with the Glu residue of the Glu-plasminogen sequence without the signal peptide as the starting amino acid), the amino acid sequence of the mini-plasminogen is represented by SEQ ID NO: 10, and the cDNA sequence encoding this amino acid sequence is represented by SEQ ID NO: 9. While micro-plasminogen comprises only a serine protease domain, and it is reported that its amino acid sequence comprises residues Ala543-Asn791 (with the Glu residue of the Glu-plasminogen sequence without the signal peptide as the starting amino acid); additionally, it is disclosed in patent document CN102154253A that its sequence comprises residues Lys531-Asn791 (with the Glu residue of the Glu-plasminogen sequence without the signal peptide as the starting amino acid); the sequence of the present patent application refers to the patent document CN102154253A, the amino acid sequence is represented by SEQ ID NO: 12, and the cDNA sequence encoding this amino acid sequence is represented by SEQ ID NO: 11.

In the present application, "plasmin" and "fibrinolytic enzyme" may be used interchangeably with the same meaning; "plasminogen" and "fibrinolytic zymogen" may be used interchangeably with the same meaning.

In the present application, "lack" of plasminogen or plasminogen activity means that the content of plasminogen in a subject is lower than that of a normal person, and is sufficiently low to affect the normal physiological function of the subject; "deficiency" of plasminogen or plasminogen activity means that the content of plasminogen in a subject is significantly lower than that of a normal person, and even the activity or expression is extremely low, and the normal physiological function may only be maintained by external supply of plasminogen.

Those skilled in the art may understand that, all technical solutions of plasminogen according to the present application are applicable to plasmin, thus the technical solutions described in the present application encompass plasminogen and plasmin. During circulation, plasminogen is present in a closed, inactive conformation, but when bound to a thrombus or cell surface, it is converted into active plasmin with an open conformation after being mediated by plasminogen activator (PA). Active plasmin may further hydrolyze the fibrin clot into degradation products of fibrin and D-dimers, thereby dissolving the thrombus. The PAp domain of plasminogen comprises an important determinant for maintaining plasminogen in an inactive closed conformation, while the KR domain may bind to a lysine residue present on a receptor and substrate. A variety of enzymes are known to act as plasminogen activators, including: tissue plasminogen activator (tPA), urokinase plasminogen activator (uPA), kallikrein, and coagulation factor XII (Hageman factor) etc.

"Plasminogen active fragment" in this application includes 1) in a plasminogen protein, an active fragment capable of binding to a target sequence in a substrate, also known as lysine-binding fragment, such as a fragment comprising Kringle 1, Kringle 2, Kringle 3, Kringle 4 and/or Kringle 5 (for the structure of plasminogen see, Aisina R B, Mukhametova L I. Structure and function of plasminogen/plasmin system[J]. Russian Journal of Bioorganic Chemistry, 2014, 40(6):590-605); 2) an active fragment exerting proteolytic function in plasminogen protein, such as a fragment comprising the plasminogen activity represented by SEQ ID NO: 14; 3) a fragment of plasminogen protein, which has both binding activity to a target sequence in a substrate (lysine binding activity) and plasminogen activity (proteolytic function). In some embodiments of the present application, the plasminogen is a protein comprising the active fragment of plasminogen represented by SEQ ID NO: 14. In some embodiments of the present application, the plasminogen is a protein with the lysine-binding fragment comprising Kringle 1, Kringle 2, Kringle 3, Kringle 4, and/or Kringle 5. In some embodiments, the plasminogen active fragment of the present application comprises SEQ ID NO: 14, or a protein with an amino acid sequence having at least 80%, 90%, 95%, 96%, 97%, 98%, 99% homology with SEQ ID NO: 14. Therefore, the plasminogen of the present application comprises a protein having the plasminogen active fragment and still retaining the plasminogen activity. In some embodiments, the plasminogen of the present application comprises Kringle 1, Kringle 2, Kringle 3, Kringle 4 and/or Kringle 5, or a protein having at least 80%, 90%, 95%, 96%, 97%, 98%, or 99% homology with Kringle 1, Kringle 2, Kringle 3, Kringle 4 or Kringle 5, and still retaining lysine binding activity.

At present, the methods for measuring plasminogen and its activity in blood comprise: detection of tissue plasminogen activator activity (t-PAA), detection of plasma tissue plasminogen activator antigen (t-PAAg), detection of plasma tissue plasminogen activity (plgA), detection of plasma tissue plasminogen antigen (plgAg), detection of the activity of plasma tissue plasminogen activator inhibitor, detection of the antigen of plasma tissue plasminogen activator inhibitor, and detection of plasma plasmin-antiplasmin complex (PAP); wherein the most commonly used detection method is the chromogenic substrate method: adding streptokinase (SK) and a chromogenic substrate to the plasma to be detected, the PLG in the plasma to be detected is converted into PLM under the action of SK, and PLM acts on the chromogenic substrate; subsequently, the detection by spectrophotometer indicates that the increase in absorbance is proportional to plasminogen activity. In addition, the plasminogen activity in blood may also be detected by immunochemical method, gel electrophoresis, immunoturbidimetry, and radioimmunoassay.

"Ortholog or orthologs" refer to homologs between different species, including both protein homologs and DNA homologs, also known as orthologs and vertical homologs; particularly it refers to proteins or genes evolved from the same ancestral gene in different species. The plasminogen according to the present application includes human natural plasminogen, and also includes plasminogen ortholog or orthologs derived from different species and having plasminogen activity.

A "conservative substitution variant" refers to a variant in which a given amino acid residue is altered without changing the overall conformation and function of the protein or enzyme, including but not limited to those variants in which the amino acid(s) in the amino acid sequence of the parent protein are replaced by amino acid(s) with similar properties (e.g., acidic, basic, hydrophobic, etc.). Amino acids with similar properties are well known in the art. For example, arginine, histidine and lysine are hydrophilic basic amino acids and are interchangeable. Similarly, isoleucine is a hydrophobic amino acid, and may be replaced by leucine, methionine or valine. Therefore, the similarity of two proteins or amino acid sequences with similar functions may differ; for example, 70% to 99% similarity (identity) based on the MEGALIGN algorithm. "Conservative substitution variants" also include polypeptides or enzymes having more than 60%, preferably more than 75%, more preferably more than 85%, or even most preferably more than 90% amino acid sequence identity determined by BLAST or FASTA algorithm, and having the same or substantially similar properties or functions as the natural or parent protein or enzyme.

"Isolated" plasminogen refers to a plasminogen protein isolated and/or recovered from its natural environment. In some embodiments, the plasminogen will be purified: (1) to more than 90%, more than 95%, or more than 98% purity (by weight), as determined by Lowry's method, e.g., more than 99% (by weight), (2) to a degree sufficient to obtain at least 15 residues of the N-terminal or internal amino acid sequence by using a spinning cup sequence analyzer, or (3) to homogeneity as determined by using Coomassie blue or silver staining through sodium dodecyl sulfate-polyacrylamide gel electrophoresis (SDS-PAGE) under reducing or non-reducing conditions. Isolated plasminogen also includes plasminogen prepared from recombinant cells by bioengineering techniques and isolated by at least one purification step.

The terms "polypeptide", "peptide" and "protein" are used interchangeably herein to refer to a polymeric form of amino acids of any length, which may include genetically encoded and non-genetically encoded amino acids, chemically or biochemically modified or derivatized amino acids, and polypeptides with modified peptide backbones. The terms include fusion proteins including, but not limited to, fusion proteins with heterologous amino acid sequences, fusions with heterologous and homologous leader sequences (with or without N-terminal methionine residues); and the like.

"Percent (%) of amino acid sequence identity" with respect to a reference polypeptide sequence is defined as, after introducing gaps as necessary to achieve maximum percent sequence identity, and no conservative substitutions are considered as part of the sequence identity, the percentage of amino acid residues in a candidate sequence that are identical to the amino acid residues in a reference polypeptide sequence. Alignment for purposes of determining percent amino acid sequence identity may be accomplished in a variety of ways within the technical scope in the art, e.g., by publicly available computer software, such as BLAST, BLAST-2, ALIGN or Megalign (DNASTAR) software. Those skilled in the art may determine the appropriate parameters for aligning sequences, including any algorithms needed to achieve maximal alignment over the full length of the sequences to be compared. However, for the purpose of the present application, the values of percent amino acid sequence identity are generated by using the computer program ALIGN-2 for sequence comparison.

Where ALIGN-2 is used to compare amino acid sequences, the percentage (%) of amino acid sequence identity of a given amino acid sequence A relative to a given amino acid sequence B (or may be expressed as a given amino acid sequence A having a certain percentage (%) of amino acid sequence identity relative to, with or with respective to a given amino acid sequence B) is calculated as follows:

$$\text{Fraction } X/Y \text{ times } 100;$$

wherein X is the number of amino acid residues scored as identical matches during the alignment of sequences A and B by the sequence alignment program ALIGN-2, and wherein Y is the total number of amino acid residues in sequence B. It should be appreciated that, where the length of amino acid sequence A is not equal to that of amino acid sequence B, the percentage (%) of amino acid sequence identity of A with respect to B will not equal to the percentage (%) of amino acid sequence identity of B with respect to A. Unless expressly stated otherwise, all the values of percentage (%) of amino acid sequence identity used herein are obtained by using the ALIGN-2 computer program as described in the preceding paragraph.

The terms "individual", "subject" and "patient" are used interchangeably herein to refer to mammals including, but not limited to, murine (rat, mouse), non-human primate, human, canine, feline, hoofed animals (e.g., horses, cattle, sheep, pigs, goats), etc.

A "therapeutically effective amount" or "effective amount" refers to an amount of plasminogen sufficient to prevent and/or treat a disease when administrated to a mammal or other subject for treating the disease. A "therapeutically effective amount" will vary depending on the component of plasminogen in use, the severity of the disease and/or symptoms thereof in the subject to be treated, as well as the age, weight, and the like.

The term "treatment" of a disease state includes inhibiting or preventing the development of the disease state or its clinical symptoms, or alleviating the disease state or symptoms, resulting in temporary or permanent regression of the disease state or its clinical symptoms.

The term "muscle strength" refers to the strength of muscle contraction during voluntary movement of a limb or the strength of a muscle during active movement. According to the situation of muscle strength, muscle strength is usually divided into the following 0-5 grades: grade 0, complete paralysis, no muscle contraction can be measured; grade 1, only muscle contraction can be measured, but no movement; grade 2, the limbs can move horizontally on the bed, but cannot resist their own gravity, i.e., they cannot be lifted off the bed surface; grade 3, the limbs can overcome gravity and can be lifted off the bed surface, but cannot resist resistance; grade 4, the limbs can do movement against external resistance, but incomplete; grade 5, normal muscle strength.

The term "muscle tone" refers to the tension of a muscle in its resting, relaxed state. Muscle tone is the basis for maintaining various postures and normal movements of the body. Muscle tone manifests itself in various forms. For example, when a person is lying down and resting, the tension of the muscles of various parts of the body is called resting muscle tone. When the body is standing, although the muscles are not significantly contracted, the muscles in the front and rear of the body also maintain a certain tension to maintain the standing posture and body stability, which is called postural muscle tone. The tension of muscles during exercise, called exercise muscle tone, is an important factor to ensure continuous and smooth muscle movement (without tremors, twitches, and spasms). In pathological conditions, muscle tone increases or decreases, affecting the normal posture or movement of human body.

Preparation of the Plasminogen According to the Present Application

Plasminogen may be isolated from nature, and purified for further therapeutic use, or it may be synthesized by standard chemical peptide synthesis techniques. When the polypeptide is synthesized chemically, the synthesis may be carried out via liquid phase or solid phase. Solid-phase polypeptide synthesis (SPPS) (in which the C-terminal amino acid of the sequence is attached to an insoluble support, followed by the sequential addition of the retaining amino acids in the sequence) is a suitable method for chemical synthesis of plasminogen. Various forms of SPPS, such as Fmoc and Boc, may be used to synthesize plasminogen. Techniques for solid-phase synthesis are described in Barany and Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85:2149-2156 (1963); Stewart et al., Solid Phase Peptide Synthesis, 2nd ed. Pierce Chem. Co., Rockford, Ill. (1984); and Ganesan A. 2006 Mini Rev. Med Chem. 6:3-10, and Camarero J A et al. 2005, Protein Pept Lett. 12:723-8. Briefly, small insoluble porous beads are treated with functional units on which peptide chains are constructed; after repeated cycles of coupling/deprotection, the attached solid-phase free N-terminal amine is coupled to a single N-protected amino acid unit. This unit is then deprotected to reveal new N-terminal amines that may be attached to other amino acids. The peptide remains immobilized on the solid phase, subsequently it is cleaved off.

Plasminogen according to the present application may be produced by standard recombinant methods. For example, a nucleic acid encoding plasminogen is inserted into an expression vector to be operably linked to regulatory sequences in the expression vector. The regulatory sequences for expression include, but are not limited to, promoters (e.g., naturally associated or heterologous promoters), signal sequences, enhancer elements, and transcription termination sequences. Expression regulation may be a eukaryotic promoter system in a vector capable of transforming or transfecting a eukaryotic host cell (e.g., COS or CHO cell). Once the vector is incorporated into a suitable host, the host is maintained under conditions suitable for high-level expression of the nucleotide sequence and collection and purification of plasminogen.

A suitable expression vector is typically replicated in a host organism as an episome or as an integrated part of the host chromosomal DNA. Typically, an expression vector contains a selectable marker (e.g., ampicillin resistance, hygromycin resistance, tetracycline resistance, kanamycin resistance, or neomycin resistance marker) to facilitate the detection of those cells transformed with desired exogenous DNA sequence.

*Escherichia coli* is an example of a prokaryotic host cell that may be used to clone a plasminogen-encoding polynucleotide. Other microbial hosts suitable for use include bacilli such as *Bacillus subtilis*, and other enterobacteriaceae such as *Salmonella, Serratia*, and various *Pseudomonas* species. In these prokaryotic hosts, expression vectors may also be generated, which typically contain an expression control sequence (e.g., origin of replication) that are compatible with the host cell. In addition, there are many well-known promoters, such as the lactose promoter system, the tryptophan (trp) promoter system, the beta-lactamase promoter system, or the promoter system from bacteriophage lambda. A promoter will typically control the expression, optionally in case of an operator gene sequence, and have ribosome binding site sequence, etc., to initiate and complete transcription and translation.

Other microorganisms, such as yeast, may also be used for expression. Yeast (e.g., *S. cerevisiae*) and *Pichia* are examples of suitable yeast host cells, and as required a suitable vector has an expression control sequence (e.g., promoter), origin of replication, termination sequence, etc. A typical promoter comprises 3-phosphoglycerate kinase and other saccharolytic enzymes. Particularly, inducible yeast promoters include promoters from ethanol dehydrogenase, isocytochrome C, and enzymes responsible for maltose and galactose utilization.

In addition to microorganisms, mammalian cells (e.g., mammalian cells grown in in vitro cell culture) may also be used to express and produce the plasminogen of the application (e.g., polynucleotides encoding plasminogen). See Winnacker, From Genes to Clones, VCH Publishers, N.Y., N.Y. (1987). Suitable mammalian host cells include CHO cell lines, various Cos cell lines, HeLa cells, myeloma cell lines, and transformed B cells or hybridomas. Expression vectors for use in these cells may comprise expression control sequences such as origin of replication, promoter and enhancer (Queen et al., Immunol. Rev. 89:49 (1986)), and necessary sites for processing information such as ribosome binding sites, RNA splicing sites, polyadenylation sites, and transcription terminator sequences. Examples of suitable expression control sequences are promoters derived from immunoglobulin gene, SV40, adenovirus, bovine papilloma virus, cytomegalovirus, and the like. See Co et al, J. Immunol. 148:1149 (1992).

Once synthesized (chemically or recombinantly), the plasminogen of the present application may be purified according to standard procedures in the art, including ammonium sulfate precipitation, affinity column, column chromatography, high performance liquid chromatography (HPLC), gel electrophoresis, and the like. The plasminogen is substantially pure, e.g., at least about 80-85% pure, at least about 85-90% pure, at least about 90-95% pure, or 98-99% pure or purer, e.g., free of contaminants such as cellular debris, macromolecules other than the plasminogen, and the like.

Medicament Formulation

A therapeutic formulation may be prepared by mixing the plasminogen of desired purity with an optional pharmaceutical carrier, excipient, or stabilizer (Remington's Pharmaceutical Sciences, 16th edition, Osol, A. ed. (1980)), to form a lyophilized formulation or an aqueous solution. An acceptable carrier, excipient, or stabilizer is non-toxic to a recipient at the employed dosage and concentration, including buffers such as phosphate, citrate and other organic acids; antioxidants such as ascorbic acid and methionine; preservatives (such as octadecyldimethylbenzylammonium chloride; hexanediamine chloride; benzalkonium chloride, benzethonium chloride; phenol, butanol or benzyl alcohol; alkyl parahydroxybenzoate such as methyl or propyl paraben; catechol; resorcinol; cyclohexanol; 3-pentanol; m-cresol); low molecular weight polypeptides (less than about 10 residues); proteins such as serum albumin, gelatin or immunoglobulins; hydrophilic polymers such as polyvinylpyrrolidone; amino acids such as glycine, glutamine, asparagine, histidine, arginine or lysine; monosaccharides, disaccharides and other carbohydrates such as glucose, mannose, or dextrin; chelating agents such as EDTA; carbohydrates such as sucrose, mannitol, fucose, or sorbitol; salt-forming counterions such as sodium; metal complexes (such as zinc-protein complexes); and/or nonionic surfactants such as TWEN™, PLURONICS™ or polyethylene glycol (PEG).

The formulations according to the present application may also contain more than one active compound as required for the particular condition to be treated, preferably those compounds are complementary in activity and do not have side effects with each other. For example, antihypertensive medicaments, antiarrhythmic medicaments, diabetes medicaments, etc.

The plasminogen according to the present application may be encapsulated in microcapsules prepared by techniques such as coacervation or interfacial polymerization, for example, the plasminogen may be placed in colloidal drug delivery systems (e.g., liposomes, albumin microspheres, microemulsions, nanoparticles and nanocapsules) or in hydroxymethyl cellulose or gel-microcapsules and poly-(methyl methacrylate) microcapsules in macroemulsions. These techniques are disclosed in Remington's Pharmaceutical Sciences 16th edition, Osol, A. Ed. (1980).

The plasminogen according to the present application for in vivo administration must be sterile. This may be easily achieved by filtration through sterilizing filters before or after lyophilization and reformulation.

The plasminogen according to the present application may be prepared as a sustained-release formulation. Suitable examples of sustained-release formulations include semi-permeable matrices of solid hydrophobic polymers which have a certain shape and contain glycoprotein, for example, membranes or microcapsules. Examples of sustained-release matrices include polyesters, hydrogels such as poly(2-hydroxyethyl-methacrylate) (Langer et al., J. Biomed. Mater. Res., 15:167-277 (1981); Langer, Chem. Tech., 12:98-105 (1982)), or poly(vinyl alcohol), polylactide (U.S. Pat. No. 3,773,919, EP58,481), copolymers of L-glutamic acid and γ-ethyl-L-glutamic acid (Sidman, et al., Biopolymers 22:547 (1983)), non-degradable ethylene-vinyl acetate (Langer, et al., supra), or degradable lactic acid-glycolic acid copolymers such as Lupron Depot™ (injectable microspheres consisting of lactic acid-glycolic acid copolymer and leuprolide acetate), and poly-D-(–)-3-hydroxybutyric acid. Polymers such as ethylene-vinyl acetate and lactic acid-glycolic acid may release molecules continuously for more than 100 days, while some hydrogels release proteins for shorter period of time. Rational strategies to stabilize proteins may be devised based on the relevant mechanisms. For example, if the mechanism of condensation is found to form intermolecular S—S bond through thiodisulfide interchange, then stabilization may be achieved by modifying sulfhydryl residues, lyophilizing from acidic solutions, controlling humidity, using suitable additives, and developing specific polymer matrix composition.

Administration and Dosage

Administration of the pharmaceutical composition according to the present application may be accomplished by different means, e.g., intravenous administration, intraperitoneal administration, subcutaneous administration, intracranial administration, intrathecal administration, intraarteral administration (e.g., via the carotid artery), and intramuscular administration.

Preparations for parenteral administration include sterile aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, or fixed oils. Intravenous vehicles include fluid and nutritional supplements, electrolyte supplements, and the like. Preservatives and other additives may also be present, such as, for example, antimicrobials, antioxidants, chelating agents, and inert gases, etc.

Dosing regimens will be determined by medical personnel based on various clinical factors. As is well known in the medical field, the dosage for any patient depends on a variety of factors, including the patient's size, body surface area, age, the particular compound to be administrated, sex, number and route of administration, general health, and other concomitantly administrated medicaments. The dosage range of the pharmaceutical composition comprising the plasminogen according to the present application may be about 0.0001-2000 mg/kg, or about 0.001-500 mg/kg (e.g., 0.02 mg/kg, 0.25 mg/kg, 0.5 mg/kg, 0.75 mg/kg, 10 mg/kg, 50 mg/kg, etc.) body weight of the subject per day. For example, the dose may be 1 mg/kg body weight, or 50 mg/kg body weight, or in the range of 1-50 mg/kg, or at least 1 mg/kg. Dosages above or below this exemplary range are also contemplated, especially in view of the factors set forth above. Intermediate doses within the above ranges are also included within the scope of the present application. Subjects may be administrated such doses daily, every other day, weekly, or according to any other schedule determined by empirical analysis. An exemplary dosage schedule includes 1-10 mg/kg on consecutive days. Real-time evaluation of therapeutic efficacy and safety is required during the administration of the medicament of the present application.

Product or Kit

One embodiment of the present application relates to a product or kit comprising plasminogen or plasmin of the present application useful in treating cardiovascular disease caused by diabetes and related disorders. The product preferably comprises a container, a label or package insert. Suitable containers are bottles, vials, syringes, etc. The container may be made of various materials such as glass or plastic. The container contains a composition which is effective for treatment of the disease or condition according to the present application and has a sterile access port (e.g., the container may be an intravenous solution pack or vial containing a stopper penetrable by a hypodermic needle). At least one active agent in the composition is plasminogen/plasmin. The label on or attached to the container indicates that the composition is used for treating cardiovascular disease caused by diabetes and related disorders mentioned in the present application. The product may further comprise a second container containing a pharmaceutically acceptable buffer, such as phosphate buffered saline, Ringer's solution, and glucose solution. It may further contain other materials required from a commercial and user standpoint, including other buffers, diluents, filters, needles and syringes. In addition, the product comprises a package insert with instructions for use, including, for example, instructing the user of the composition to administrate the composition comprising plasminogen to the patient along with other medicaments for treatment of concomitant diseases.

EXAMPLES

The human plasminogen used in all the following examples was obtained from the plasma of the donor, and was purified from the plasma of the human donor based on the method described in the References [1-3] with process optimization, wherein the human Lys-plasminogen and Glu-plasminogen>98%.

All patients in the following Examples 1-7 signed an informed consent, voluntarily received the above-mentioned treatment of plasminogen purified from human plasma, and obtained the approval of the hospital ethics committee. The administration regimen and dosage are adjusted according to the severity and course of the disease. The mode of administration is aerosol inhalation or intravenous injection. The drug concentration of aerosol inhalation and intravenous injection is 5 mg/ml, and normal saline is used as vehicle.

Example 1: Type II SMA Patient

Female patient, 38 months old. At 10 months old, she was unable to crawl, her legs were weak, and her motor ability barely improved after 1 year of age. At the age of 1 year and 9 months, she was diagnosed with SMA by genetic testing, muscle strength was grade 2, and her lower limbs could not carry weight. Then she started taking salbutamol, methylcobalamin, and coenzyme Q10. At the age of 2 years, her motor ability further degenerated so that she could not climb, and could only sit and stand for a short time. At the age of 2 years and 2 months, she started mesenchymal stem cell therapy, and the balance ability was improved and not easy to get sick, but she still could not stand. At the age of 2 years and 11 months, she started acupoint injection of the mouse nerve growth factor, then the balance ability was improved, the lower limbs began to have supporting strength, and the measured muscle strength reached grade 3.

Administration Regimen

Intravenous injection; dosage: 100-200 mg/time; frequency: once every other day, once every other 2 days, or once every other 3 days; 2 weeks as a course of treatment; 2-3 weeks between adjacent courses of treatment. A total of 6 courses of treatment were performed.

The Expanded Hammersmith Functional Motor Scale (HFMSE) is designed to assess motor function in patients with type II and type III SMA, reflecting the disease severity. The functional motor scale is defined as change from baseline to assess changes in motor function in children; the higher the scores, the better the motor function [4-6].

Nerve electromyography (EMG) is the main diagnosis and identification means for motor neuron disease, and the amplitude of compound muscle action potential reflects the neuronal axon injury. SMA is a degenerative motor neuron disease with massive motor neuron death, exhibiting muscle weakness and reduced or even undetectable compound muscle action potential amplitudes [7].

Therapeutic Efficacy

HFMSE scores: the score before treatment was 20 points, and the score after the first course of treatment was 21 points. The score before the second course of treatment was 23 points, and the score after treatment was 24 points. The score after the sixth course of treatment was 25 points.

Motor function evaluation: before treatment, the patient could not stand without assistance. After 2 courses of treatment, the patient was able to stand with assistance. After 3 courses of treatment, the patient achieved assisted walking, and the patient's head control ability was significantly improved. With the progress of treatment, the patient's motor function was further improved, including prolonged standing time with assistance and increased walking distance with assistance.

Figure 1:
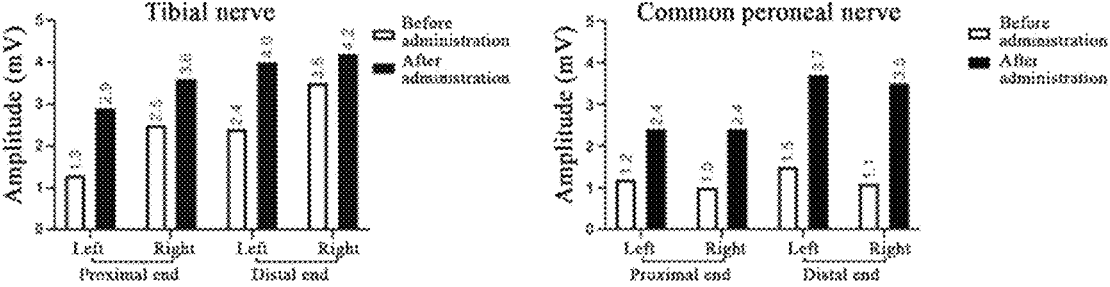
FIG. 1 shows the results of motor nerve electromyographic amplitudes before and after treatment of the type II SMA patients in Example 1. The results show that, the action potential amplitudes of the tibial nerve and common peroneal nerve in the patients are increased to varying degrees, as compared with those before treatment. The results show that, plasminogen may improve the conduction function of peripheral neurons and alleviate neuromuscular injury in patients with type II SMA.

EMG: the action potential amplitudes of bilateral tibial nerves, common peroneal nerve and femoral nerve were significantly increased after treatment, as compared with those before treatment (FIG. 1).

In addition, the patient's mental state was significantly improved and the vitality increased after the treatment. There were no drug-related side effects during the treatment.

The above results indicate that, plasminogen may improve the HFMSE score of a patient with type II SMA, and improve the motor function, neuromuscular function, and mental state of the patient.

Example 2: Type II SMA Patient

Male patient, 30 months old. There was no abnormality after birth. At the age of nine months, he could not stand independently and turn over on his own; his hands occasionally trembled slightly, could not grasp and raise his head. At the age of ten months, the patient was diagnosed with type II SMA by genetic testing. At the age of 1-2 years, he started to rehabilitate in the rehabilitation center, once a week; then he could keep sitting alone, grab light objects with both hands, stretch his calf slowly, and complete turning over with assistance. At the age of 2 years and 2 months, intravenous infusion of bone marrow mesenchymal stem cells was administered three times, two units each time; and the improvement was not significant. At the age of 2 years and 4 months, the neural stem cells were injected twice, two units each time; and the improvement was obvious after the injection. Status: he can sit independently, when sitting alone, the body can lean slightly to the sides and support the body with both hands, but the arms cannot be raised. Head control has been improved, and he can quickly shake head back and forth, and keep his head up by four-point support with the parent's assistance. The strength of the legs is increased, and the calf can be kicked back and forth while sitting on the seat. He may lean on the parent to maintain a standing position with slight knee assistance.

Administration Regimen

The first time: intravenous injection, 50 mg; the second time: intravenous injection, 50 mg; the third and fourth time: intravenous injection, 100 mg. The administration frequency is once every other 2 days, or once every other 3 days for 2 weeks.

Therapeutic Efficacy

Figure 2:
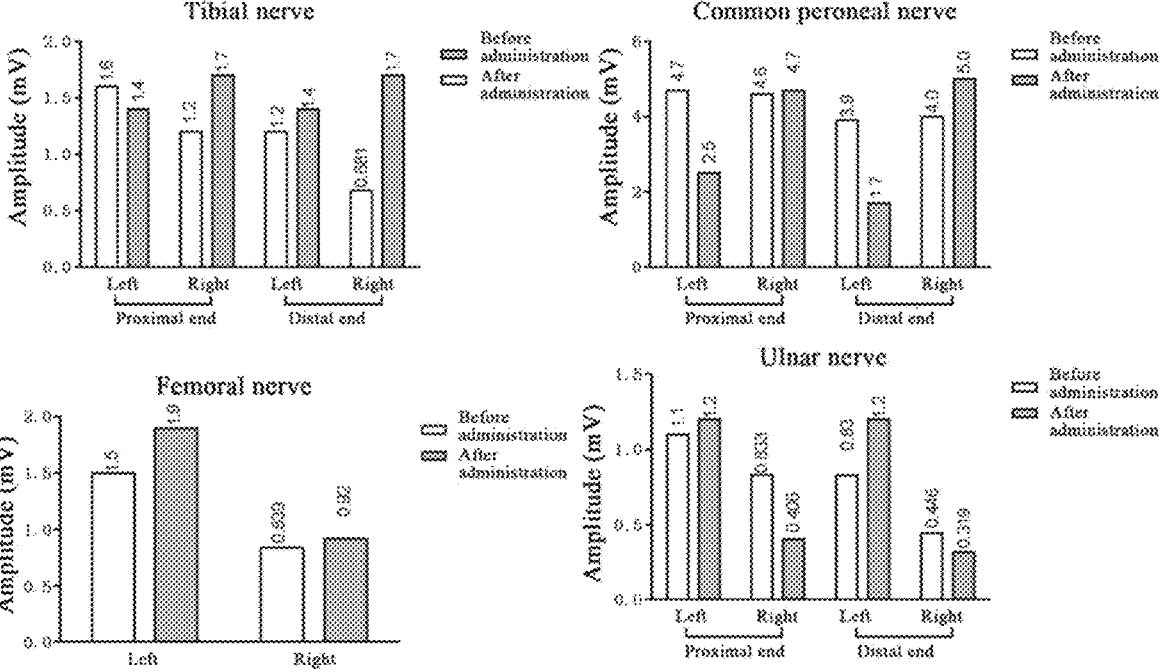
FIG. 2 shows the results of motor nerve electromyographic amplitudes of the upper and lower limbs before and after treatment of the patients in Example 2. The action potential amplitudes of the left femoral nerve, right ulnar nerve, bilateral common peroneal nerves and tibial nerve in the patients are increased to varying degrees, as compared with those before treatment. The results show that, plasminogen may improve the conduction function of peripheral neurons and alleviate neuromuscular injury in patients with type II SMA.

The HFMSE score was 2 points before the treatment, and the HFMSE score was 8 points after the fourth treatment, and the patient could sit independently and raise both hands. The electromyography results show that, the amplitudes of the action potentials of the left femoral nerve, right ulnar nerve, common peroneal nerve and tibial nerve are increased after treatment, as compared with those before treatment (FIG. 2).

The above results indicate that, plasminogen can improve the HFMSE score of a patient with type II SMA, improve the motor function, and improve the neuromuscular function of the patient, and there are no drug-related side effects during the treatment.

Example 3: Type II SMA Patient

Female patient, 24 months old. At the age of 1 year, she could stand with support, was unable to climb on four-point support. At 16 months old, the electromyography showed neurogenic injury, and the patient was diagnosed with type II SMA by genetic testing. Status: Unstable sitting alone, unable to sit up while lying down, able to stand up with handrail, stand up by leaning, and walk with handrail; sometimes the status was in good condition, and sometimes in bad condition, she was difficult to lift both hands.

Administration Regimen

Intravenous injection; dosage: 50 mg-100 mg each time; frequency: once every other day, or once every other 3 days; 2 weeks is a course of treatment, and 3-4 weeks between adjacent courses of treatment, with a total of 8 courses of treatment.

Therapeutic Efficacy

HFMSE scores: the score before treatment was 23 points, and the score after the first course of treatment was 24 points. There was an interval of approximately two months between the patient's first and second courses of treatment. The score before the second course of treatment was 23 points, and the score after the treatment was 24 points. The score after the eighth course of treatment was 28 points.

Motor function evaluation: before treatment, the patient could not raise the hands above head. After 2 courses of treatment, the patient achieved standing without assistance and walking with assistance, and he was able to raise his hands above his head. After continuous administration, the patient's motor function was further improved, and was capable of sitting independently, standing with handrail, and stably walking with handrail; and the time for these activities was gradually extended.

Figures 3, 4A, 4B, 5:
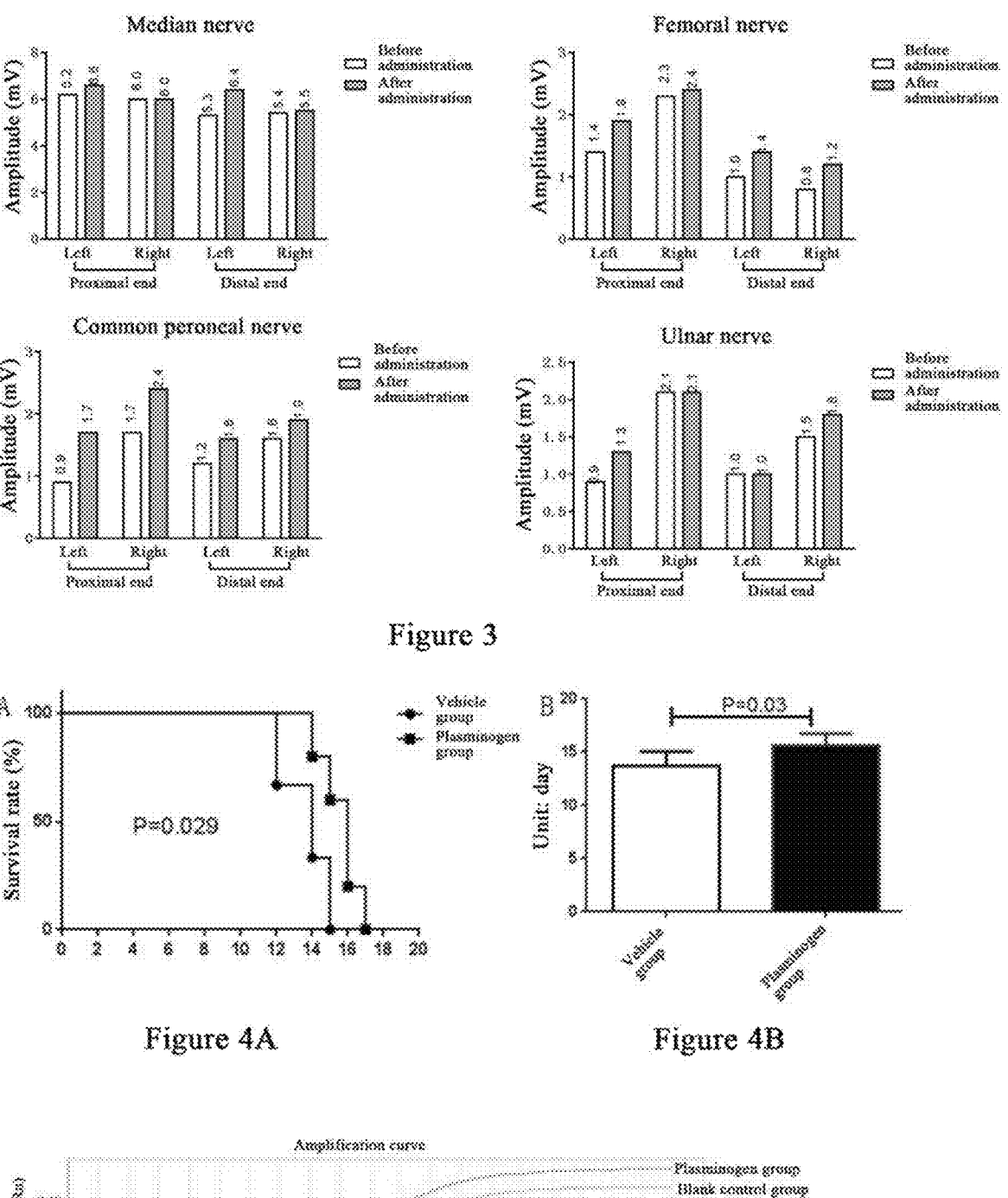
FIG. 3 shows the results of motor nerve electromyographic amplitudes of the upper and lower limbs before and after treatment of the patients in Example 3. The action potential amplitudes of bilateral median nerves, tibial nerve, common peroneal nerve and ulnar nerve in the patients are increased to varying degrees, as compared with those before treatment. The results show that, plasminogen may improve the conduction function of peripheral neurons, and alleviate neuromuscular injury in patients with type II SMA.
FIGS. 4A-4B show the statistical results of survival curve and survival time of SMNΔ7 SMA mice after administration of plasminogen.
FIG. 5 shows the results of qPCR detection of SMN gene in spinal cord of SMNΔ7 SMA mice after administration of plasminogen. The results show that, the spinal cords of the mice in the blank control group have a certain level of SMN gene transcription, the level of SMN gene transcription in the mice in the vehicle group is lower than that in the mice

EMG: after treatment, the action potential amplitudes of bilateral median nerve, tibial nerve, common peroneal nerve, and ulnar nerve all increased to varying degrees (FIG. 3).

In addition, no drug-related side effects were observed during the treatment.

The above results indicate that, plasminogen can improve the HFMSE score, motor function and neuromuscular function of a patient with type II SMA.

Example 4: Type II SMA Patient

Male patient, 43 months old. At the age of 12 months, the electromyography detection showed neurogenic injury, and at the age of 14 months he was diagnosed with type II SMA by genetic testing. By the age of 24 months, he degenerated to a status that he could not sit independently, and could only sit by leaning. At the age of 29 months, he started taking salbutamol, methylcobalamin, and coenzyme q10, and his motor function was gradually and slightly improved. At the age of 36 months, he started treatment with mesenchymal stem cells, and totally received 5 injections of mesenchymal stem cells intravenously. After the injection of mesenchymal stem cells, the patient's overall state was improved significantly, his mental state was improved, he was not easy to get tired and get sick, but he was still not able to stand. At the age of 38 months, acupoint injection of mouse nerve growth factor was performed, but there was no obvious effect.

Administration Regimen

The first time: intravenous injection, 50 mg; the second time: intravenous injection, 50 mg; the third time: intravenous injection, 100 mg; the fourth time: intravenous injection, 150 mg, the administration was performed every other 3 days, for 2 weeks.

Therapeutic Efficacy

The patient's right arm function was improved after treatment, and the patient could lift his right arm to 90 degrees without help of the left hand, but the HFMSE score was not improved. There were no drug-related side effects during the treatment.

Example 5: Type II SMA Patient

Male patient, 26 months old. At the age of 10 months, he was diagnosed with SMA by genetic testing, and the copy number of SMN2 (survival motor neuron gene 2) was 3. At the age of 12 months, he lost the ability of turning over, his arms were unable to support his body, he could only lie on the bed completely, and his fingers could not exert force on their own. At the age of 13 months, he started the injection of umbilical cord mesenchymal stem cells. After the injection of stem cells, the strength of the legs was increased, the breathing was improved, and the quality of sleep was also improved. At the age of 16 months, he started taking Chinese medicine. After the comprehensive treatment of mesenchymal stem cells, traditional Chinese medicine and rehabilitation training, the patient could sit independently and keep the balance by himself, but he was unable to turn left or right or pick up toys on his left or right. He was able to roll over independently, and the leg strength was increased significantly, breathing was improved, and voice became louder, the pectus excavatum was improved significantly, rib valgus signs were improved, and strength of the arms and hands was increased, but still could not be pulled up by grasping an adult's hand. The arm lift was degenerated in some way, and the arm could be raised to the top of the head by itself before, but only to the face when the following treatment was started.

Administration Regimen

Intravenous injection for two weeks, once every other day, 4 times administration in the first week with the doses of 10 mg, 20 mg, 30 mg, and 40 mg respectively; 4 times administration in the second week with the doses of 50 mg, 50 mg, 100 mg, and 100 mg respectively.

Therapeutic Efficacy

Calf and ankle strength was increased after the second administration in the first week. Nine days after the two-week treatment, strength of the hands and arms was increased, and the grasping power was increased by 50%. There were no drug-related side effects during the treatment.

These results suggest that, plasminogen can improve motor function in a patient with type II SMA.

Example 6: Type I SMA Patient

Male patient, 11 months old. He was diagnosed with type I SMA by genetic testing at 6 months old; the doctor informed that the average life cycle of patients with this type of disease was 2 years old at the time of diagnosis, and the family members did not take any treatment measures. Symptoms: weak head support; weak upper limbs and arms and inability to lift, less hand swing, weak grasping, weak middle finger; weak lower limbs, less swinging, movable toes; unable to sit independently, unable to turn over independently, weak sucking, difficulty in swallowing; blood oxygen monitoring was performed 24 hours a day, blood oxygen saturation was 92-97%, and the chest rose and fell weakly when breathing.

Administration Regimen

Aerosol inhalation (2-3 times/day)+intravenous bolus injection (once per 3 days), the treatment cycle was ten courses of treatment (2 weeks as a course of treatment). Adjacent courses of treatment were separated by 2 weeks. The aerosol inhalation dose was 5-10 mg, and the intravenous dose was 50-200 mg.

The CHOP INTEND scale (Children's Hospital of Philadelphia Test Scale for Infant Neuromuscular Diseases) was used to evaluate the improvement of motor function in patients with type I SMA. A higher score indicates better motor function [8].

Therapeutic Efficacy

Survival status: after 10 courses of treatment, the patient was older than 25 months, exceeding the 10-month survival time for most patients shown by natural history studies of patients with type I SMA [9]. In addition, this study found that the mental state and growth and development (height, weight, chest circumference) of a patient with SMA were significantly improved, and compared with a patient of the same age who was not treated with plasminogen, muscle atrophy in a patient treated with plasminogen was also improved significantly, and the typical signs of thoracic collapse in SMA were improved significantly. In addition, in the study a significant improvement in sleep status was also observed in the patient treated with plasminogen.

CHOP INTEND scores: CHOP INTEND score was 30 points before treatment, and the score increased to 50 points after 5 courses of treatment. For some reason, the 5th and 6th courses were separated by about 2 months, and the score dropped to 36 points, and the score was 44 points after the 6th course of treatment. The 6th and 7th courses were separated by about 2 months. The score was 44 points before the 7th course of treatment, and 45 points after the treatment. After the 10th course of treatment, the score was 46 points.

Motor function: after the first course of treatment, the patient was able to sit independently with head support for about 30 seconds. After the 4th course of treatment, the time of sitting independently was prolonged, about 30 seconds. With progress of the treatment, the patient's motor function continued to improve, the hand grasped strongly, the arm could be lifted slightly and voluntarily, and the foot movement and swing frequency were increased.

Swallowing function: after administration, the number of times of choking when eating and drinking was reduced, and the speaking function was good.

Respiratory function: On day 2 of the first course of treatment, the patient's blood oxygen saturation reached 97-98%, occasionally 95-96%. After 2 courses of treatment, the patient's breathing strength increased. After 10 courses of treatment, the patient was more than 25 months old, and the patient still maintained a good breathing state without ventilatory support. The natural history study of type I SMA showed that without ventilatory support, the survival rate at 20 months old was only 8% [10].

The above results indicate that, plasminogen can improve the CHOP INTEND score and motor function of a patient with type I SMA, and can achieve a milestone improvement of sitting without support for 30 seconds and head support for 30 seconds; it can also improve patients' swallowing function and speaking ability, improve the patient's thoracic collapse signs, improve lung function, increase blood oxygen saturation, and improve the patient's mental state and sleep.

Example 7: Non-5q SMA Patient

Female patient, 40 months old (3 years and 4 months). The onset of the disease was at 6 months, and she was diagnosed with non-5q SMA by genetic testing at the age of 1.5 years (18 months old). Due to lung infection and difficulty in expelling sputum to block the respiratory tract, resulting in weakness of breathing, and gradually spontaneous respiratory failure after intermittent use of the ventilator, unable to breath without ventilator, using ventilator for about 1.5 years; loss of language function, facial paralysis, immobility, muscle strength grade 0. Symptoms: since the use of the ventilator, daily use of expectoration machines, sputum suction devices, oxygen inhalation, atomization (twice a day), and nasal feeding. The electromyography results showed that, the motor neurons of both upper and lower limbs were severely injured, and no action potential was observed.

Administration Regimen

The first course of treatment (2 weeks): aerosol inhalation, 10 mg/time, 3 times/day, combined with 50-100 mg intravenous injection, once every 3 days.

The second course of treatment was carried out 2 months after completion of the first course of treatment.

The second to fourth courses (2 weeks between adjacent courses): intravenous injection, once every other 2 days, the dose was 150 mg-250 mg.

Therapeutic Efficacy

The first course of treatment: the time of hands hanging and shaking was increased, the amplitude and the strength were increased, and the left upper arm was able to move inwardly with the assistance of support. The lower extremity was able to bend and stand up for 30 minutes with assistance, the facial expressions were increased, the eyes could blink, and the mouth could twitch voluntarily.

The second course of treatment: she could occasionally swallow soup, and her sleep was improved.

The third course of treatment: defecation was normal, the head could be shaken from side to side, and the head could be held for a few seconds with auxiliary support. The wrist was slightly strong, the fingertips could be rotated cyclically, and the left arm could be swayed autonomously with larger amplitude. Blood oxygen was maintained at 97% and no oxygen was given.

The fourth course of treatment: the coordination of the left arm was better, and the movement range of the right arm was small, but the swing frequency was fast. The muscles of the lower limbs were soft and not stiff, the facial expressions were increased, and she was able to defecate voluntarily.

Through the treatment, it was found that the patient's mental state was significantly improved, the breathing ability was significantly enhanced, and the need for ventilation support was gradually reduced.

The results show that, plasminogen can improve the motor function of a patients with non-5q SMA, including increasing in the strength, amplitude and range of limb movements, and enriching the patient's facial expressions; improving the patient's lung function and respiratory function, reducing oxygen infusion, and increasing blood oxygen saturation; improving the patient's swallowing function; improving the patient's sleep quality.

The following Examples 8-15 are administration studies on animal models, and the plasminogen is still the above-mentioned plasminogen protein purified from human donor plasma.

FVB.Cg-Grm7Tg(SMN2)89Ahmb Smn1tm1MsdTg (SMN2*delta7)4299Ahmb/J gene mutant mice (hereinafter referred to as SMNΔ7 SMA mice) have SMN1 gene homozygous mutation, and express human SMN2 gene. The clinical and pathological manifestations of the mice are similar to human SMA. The breeding mice were purchased from Jackson Laboratory in the United States (pedigree number: 005025).

Example 8: Plasminogen Prolongs the Survival Time of SMA Model Mice

SMNΔ7 SMA mice were weighed at birth, and randomly divided into vehicle group (6 mice) and plasminogen group (5 mice) according to body weight. The mice were given plasminogen after 3 days of birth. The mice in the vehicle group were intraperitoneally injected with 6 ml/kg of vehicle every day, and the mice in the plasminogen group were intraperitoneally injected with 60 mg/kg of plasminogen every day. The survival of the mice was recorded.

The statistical results of survival curve showed that, plasminogen can significantly improve the survival curve of SMNΔ7 SMA mice, and the statistical difference is significant (P=0.029). The statistical results of survival time showed that, the median survival time of the mice in the vehicle group is 14 days, and all mice died on day 15; the median survival time of the mice in the plasminogen group is 16 days, and all the mice died on day 17, and the difference of statistical analysis is significant (P=0.03), indicating that plasminogen can prolong the survival time of SMA model mice, as shown in FIGS. 4A and 4B.

Example 9: Plasminogen Promotes the Transcription of SMN Gene in Spinal Cord of SMA Model Mice Two 3-day-old SMNΔ7 SMA mice were taken, one mouse was in the vehicle group and was given 6 μl of bovine serum albumin solution (5 mg/ml) by intraperitoneal injection once in the morning and once in the afternoon each day; another mouse was in the plasminogen group and was given plasminogen by intraperitoneal injection (as per 30 μg/6 μl) once in the morning and once in the afternoon each day. One wild-type (FVB) mouse was taken as blank control group, and 6 μl of bovine serum albumin solution (5 mg/ml) was given by intraperitoneal injection once in the morning and once in the afternoon each day. The administration was performed for 9 consecutive days. The spinal cord was harvested after sacrificing the mice, and all SMN gene transcripts were detected by qPCR. The forward primer was F: GCGGCGGCAGTGGTGGCGGC (SEQ ID NO: 15); the reverse primer was R: AGTAGATCGGACAGATTTTGCT (SEQ ID NO: 16).

The results show that, the spinal cord of the mice in the blank control group has a certain level of SMN gene transcription, the level of SMN gene transcription in the mice of the vehicle group was lower than that in the mice of the blank control group, and the level of SMN gene transcription in the mice of the plasminogen group was significantly higher than that in the mice of the vehicle group and the blank control group (FIG. 5). The results suggest that plasminogen can promote SMN gene transcription.

Example 10: Plasminogen Promotes the Increase of NF-κB Level in the Brain of SMA Model Mice Seven 3-day-old SMNΔ7 SMA mice were taken. 4 mice were in the vehicle group, for the first 9 days, 6 μl of bovine serum albumin solution (5 mg/ml) was given by intraperitoneal injection once in the morning and once in the afternoon each day; starting from day 10, 6 μl of bovine serum albumin solution (10 mg/ml) was given by intraperitoneal injection once every day. 3 mice were in the plasminogen group, for the first 9 days, plasminogen was given by intraperitoneal injection (as per 30 μg/6 μl) once in morning and once in the afternoon each day; starting from day 10, and plasminogen was injected as per 60 μg/6 μl by intraperitoneal injection once a day. 4 wild-type mice were taken as blank control group, for the first 9 days, 6 μl of bovine serum albumin solution (5 mg/mi) was administered by intraperitoneal injection once in the morning and once in the afternoon; starting from day 10, 6 μl of bovine serum albumin solution (10 mg/ml) was administered by intraperitoneal injection once a day. On day 12, the mice were sacrificed to collect brain tissue, and the brain tissue homogenate was prepared for Western blot detection of NF-κB protein. 10% gels were prepared according to the dispensing instructions of the SDS-PAGE gel preparation kit (Solarbio, P1320). Samples in each group were taken to respectively mix well with 4× loading buffer (TaKaRa, e2139) at a volume ratio of 3:1, heating at 100° C. for 5 min, cooling and centrifuging for 2 min, and then 20 μL of the mixture was taken for loading. The electrophoresis conditions running at 30V for 30 min, and then running to the bottom of the gel at 100V. After electrophoresis, the gel was stripped and transferred to an activated PVDF membrane (GE, A29433753), and the electrotransfer conditions were 15V for 2.5 h. The transferred PVDF membrane was immersed in blocking solution (5% skim milk) and blocked overnight in a 4° C. refrigerator.

After washing 4 times with TBST (0.01M Tris-NaCl, pH 7.6 buffer), rabbit anti-mouse NF-κB antibody (Cell Signaling Technology, 8242) was added to incubate at room temperature for 3 h; after washing 4 times with TBST, goat anti-rabbit IgG (HRP) antibody (Abeam, ab6721) secondary antibody was added to incubate at room temperature for 1 h, washing 4 times with TBST, then placing the PVDF membrane on a clean imaging plate and adding Immobilon Western HRP Substrate (MILLIPORE, WBKLS0100) for color development, photographing under a biomolecular imager, and then Image J software was used to obtain the optical density value of each band for quantitative analysis.

Nuclear factor kappa-B (NF-κB) is a key nuclear transcription factor. NF-κB family members mainly include RelA (p65), c-Rel, RelB, NF-κB1 (p50 protein and its precursor p105) and NF-κB2 (p52 protein and its precursor p100), each member can form homologous or heterologous dimers to function. Most commonly in mammalian cells, p65 binds to p50 to form a p65/p50 dimer. In unstimulated cells, the NF-κB transcription factor binds to the inhibitory IκB (inhibitor of kappa B) protein and is thus retained in the cytoplasm. The stimulation of upstream signals leads to the phosphorylation of IκB protein under the action of IKK (IκB kinase), which is then recognized by the ubiquitin ligase complex, thereby promoting the degradation of IκB protein in a proteasome-dependent manner, and then the NF-κB is released to enter the nucleus and initiate the expression of target genes [11]. NF-κB can be found in almost all animal cells, and they are involved in the response of cells to external stimuli, and play a key role in cellular inflammatory response, immune response and other processes. NF-κB is also related to synaptic plasticity and memory [12].

The results show that, the brains of the mice in the blank control group have a certain amount of NF-κB protein, the level of NF-κB protein in the brains of the mice in the vehicle group is lower than that of the mice in the blank control group, and the level of NF-κB protein in the brains of the mice in the plasminogen group is significantly higher than that of the mice in the vehicle group, and the statistical difference is close to significant (P=0.05) (FIG. 6). These results suggest that plasminogen can promote the increase of NF-κB protein level in brain tissue of SMNΔ7 SMA mice.

Example 11: Plasminogen Promotes the Increase of NF-κB Level in Muscle of SMA Model Mice Muscles were obtained from the sacrificed mice in Example 10 above, and Western blot detection of NF-κB protein was performed according to the method described in Example 10 above.

The results show that, the muscles of mice in the blank control group have a certain amount of NF-κB protein, the level of NF-κB protein in the muscles of mice in the vehicle group is lower than that of the mice in the blank control group, and the level of NF-κB protein in the muscles of mice in the plasminogen group is significantly higher than that of the mice in the vehicle group, and the statistical difference is significant (* indicates P<0.05) (FIG. 7). These results suggest that plasminogen can promote the increase of muscle NF-κB protein level in SMNΔ7 SMA mice.

Example 12: Plasminogen Promotes the Increase of SMN Protein Level in Brain Tissue of SMA Model Mice Two 3-day-old SMNΔ7 SMA mice were taken, one mouse was in vehicle group and was given 6 μl bovine serum albumin solution (5 mg/ml) by intraperitoneal injection once in the morning and once in the afternoon each day; another mouse was in plasminogen group and was given plasminogen by intraperitoneal injection (as per 30 μg/6 μl) once in the morning and once in the afternoon each day. 2 wild-type (FVB) mice were taken as the blank control group, and 6 μl of bovine serum albumin solution (5 mg/ml) was given to each mouse by intraperitoneal injection once in the morning and once in the afternoon each day. After 9 days of administration, the mice were sacrificed to collect brain tissue, and the brain tissue homogenate was prepared for Western blot detection of SMN protein. 12% gels were prepared according to the dispensing instructions of SDS-PAGE gel. Samples in each group were taken to respectively mix well with 4× loading buffer (TaKaRa, e2139) at a volume ratio of 3:1, heating at 100° C. for 5 min, cooling and centrifuging for 2 min, and then 20 μL of the mixture was taken for loading. The electrophoresis conditions: running at 30V for 30 min, and then running to the bottom of the gel at 100V. After electrophoresis, the gel was stripped and transferred to an activated PVDF membrane (GE, A29433753), and the electrotransfer conditions were 15V for 2.5 h. The transferred PVDF membrane was immersed in blocking solution (5% skim milk) and blocked overnight in a 4° C. refrigerator. After washing 4 times with TBST (0.01M Tris-NaCl, pH 7.6 buffer), rabbit anti-mouse SMN antibody (Proteintech, 11708-1-AP) was added to incubate at room temperature for 3 h; after washing 4 times with TBST, goat anti-rabbit IgG (HRP) antibody (Abeam, ab6721) secondary antibody was added to incubate at room temperature for 1 h, washing 4 times with TBST, then placing the PVDF membrane on a clean imaging plate and adding Immobilon Western HRP Substrate (MILLIPORE, WBKLS0100) for color development, photographing under a biomolecular imager, and then Image J software was used to obtain the optical density value of each band for quantitative analysis.

The results show that, the brain of the mice in the blank control group expresses a certain amount of SMN protein, the expression level of SMN protein in the mice in the vehicle group is lower than that in the mice in the blank control group, and the expression level of SMN protein in the mice in the plasminogen group is significantly higher than that in the mice in the vehicle group (FIG. 8). These results suggest that plasminogen can promote expression of the SMN protein in brain of the SMNΔ7 SMA mice.

Example 13: Plasminogen Promotes the Increase of SMN Protein Level in Muscle of SMA Model Mice The hindlimb muscle tissue was collected from the sacrificed mice described in Example 12, and the tissue homogenate was prepared for Western blot detection of SMN protein. The detection method was as described in Example 12.

The results show that, the muscles of the mice in the blank control group express a certain amount of SMN protein, the expression level of SMN protein in the muscles of the mice in the vehicle group is lower than that of the mice in the blank control group, and the expression level of SMN protein in the muscles of the mice in the plasminogen group is significantly higher than that of the mice in the vehicle group (FIG. 9). These results suggest that, plasminogen can promote the expression of SMN protein in muscles of the SMNΔ7 SMA mice.

Example 14: Plasminogen Promotes the Formation of Mature NGF in the Brain Tissue of SMA Model Mice Brain tissue was collected from the sacrificed mice in Example 12, tissue homogenate was prepared for Western blot detection of NGF protein. 12% gels were prepared according to the dispensing instructions of SDS-PAGE gel. Samples in each group were taken to respectively mix well with 4× loading buffer (TaKaRa, e2139) at a volume ratio of 3:1, heating at 100° C. for 5 min, cooling and centrifuging for 2 min, and then 20 µL of the mixture was taken for loading. The electrophoresis conditions: running at 30V for 30 min, and then running to the bottom of the gel at 100V. After electrophoresis, the gel was stripped and transferred to an activated PVDF membrane (GE, A29433753), and the electrotransfer conditions were 15V for 2.5 h. The transferred PVDF membrane was immersed in blocking solution (5% skim milk) and blocked overnight in a 4° C. refrigerator. After washing 4 times with TBST (0.01M Tris-NaCl, pH 7.6 buffer), rabbit anti-mouse NGF antibody was added to incubate at room temperature for 3 h; after washing 4 times with TBST, goat anti-rabbit IgG (HRP) antibody (Abeam, ab6721) secondary antibody was added to incubate at room temperature for 1 h, washing 4 times with TBST, then placing the PVDF membrane on a clean imaging plate and adding Immobilon Western HRP Substrate (MILLIPORE, WBKLS0100) for color development, photographing under a biomolecular imager, and then Image J software was used to obtain the optical density value of each band for quantitative analysis.

Nerve growth factor (NGF) is an important member of the neurotrophic factor family, and it is synthesized in vivo in precursor form, including signal peptide, leader peptide, and mature peptide. Studies have reported that the precursor of nerve growth factor NGF (ProNGF) plays an opposite role relative to NGF which is formed by cleavage of ProNGF. ProNGF may promote neuronal apoptosis, while mature NGF is involved in regulating the growth, development, differentiation, survival and repair of nerve cells after injury, and also plays an important role in regulating the functional expression of central and peripheral neurons [12]. NGF/ProNGF ratio=NGF optical density (OD) value/ProNGF optical density (OD) value.

The results show that, the brain tissue of the mice in the blank control group has a certain ratio of NGF/ProNGF, and the ratio of NGF/ProNGF in the brain tissue of the mice in the plasminogen group is significantly higher than that of the mice in the vehicle group, and the statistical difference is extremely significant (*** indicates P<0.001) (FIG. 10), indicating that plasminogen can promote the transformation of ProNGF into NGF and the formation of mature NGF in SMA model mice.

Example 15: Plasminogen Ameliorates Lung Tissue Injury in SMA Model Mice

Lung tissue was collected from the sacrificed mice in Example 12, and fixed in 10% neutral formalin for 24 hours. The fixed lung tissue was dehydrated with alcohol gradient and cleared with xylene before being embedded in paraffin. The thickness of the tissue section was 5 µm. The sections were dewaxed, rehydrated, stained with hematoxylin and eosin (H&E staining), differentiated with 1% hydrochloric acid alcohol, returned to blue with ammonia, and dehydrated with alcohol gradient to seal the sections. The sections were observed under a microscope at 200×.

The results show that, the terminal bronchiolar epithelial cells of the lung tissue of the mice in the blank control group are neatly arranged and clearly distinguishable; the alveolar cavities are uniform in size, the alveolar septum is not thickened, and there is no inflammatory cell infiltration around the blood vessels; as for the lung tissue of the mice in the vehicle group, the respiratory bronchiolar epithelium is fallen off, the alveolar ducts and alveolar sacs are enlarged, the alveolar septum is widened, the alveoli collapse to structural disorder, and there are eosinophils, foam cells, and lymphocytes around the pulmonary blood vessels; the respiratory bronchiolar epithelium of the mice in the plasminogen group are arranged in an orderly manner, the alveolar ducts and alveolar sacs are enlarged, and the alveolar cavities are evenly enlarged, but the alveolar wall composed of a single layer of alveolar epithelium is visible (FIG. 11), indicating that plasminogen can ameliorates lung tissue injury in SMA model mice.

REFERENCES

[1] KENNETH C. ROBBINS, LOUIS SUMMARIA, DAVID ELWYN et al. Further Studies on the Purification and Characterization of Human Plasminogen and Plasmin. Journal of Biological Chemistry, 1965, 240 (1):541-550.

[2] Summaria L, Spitz F, Arzadon L et al. Isolation and characterization of the affinity chromatography forms of human Glu- and Lys-plasminogens and plasmins. J Biol Chem. 1976 Jun. 25; 251(12):3693-9.

[3] HAGAN J J, ABLONDI F B, DE RENZO E C. Purification and biochemical properties of human plasminogen. J Biol Chem. 1960 April; 235:1005-10.

[4] Main M, Kairon H, Mercuri E, Muntoni F. The Hammersmith functional motor scale for children with spinal muscular atrophy: a scale to test ability and monitor progress in children with limited ambulation. Eur J Paediatr Neurol. 2003; 7(4):155-9.

[5] O'Hagen J M, Glanzman A M, McDermott M P, Ryan P A, Flickinger J, Quigley J, Riley S, Sanborn E, Irvine C, Martens W B, et al. An expanded version of the Hammersmith Functional Motor Scale for SMA II and III patients. Neuromuscul Disord. 2007; 17(9-10):693-7.

[6] Mercuri E, Messina S, Battini R, Berardinelli A, Boffi P, Bono R, Bruno C, Carboni N, Cini C, Colitto F, et al. Reliability of the Hammersmith functional motor scale for spinal muscular atrophy in a multicentric study. Neuromuscul Disord. 2006; 16(2):93-8.

[7] Kelly J J, Thibodeau L, Andros P A. Use of electrophysiological tests to measure disease progression in ALS therapeutic trials[J]. Muscle Nery e, 1990, 13(3):471.

[8] Glanzman A M, Mazzone E, Main M, Pelliccioni M, Wood J, Swoboda K J, et al. The Children's Hospital of Philadelphia Infant Test of Neuromuscular Disorders (CHOP INTEND): test development and reliability. Neuromuscul Disord 2010; 20:155-161.

[9] Sithara Ramdas, Laurent Servais. New treatments in spinal muscular atrophy: an overview of currently available data. Expert Opin Pharmacother. 2020 February; 21(3):307-315.

[10] Linda P. Lowes, Lindsay N. Alfano, W. David et al. Impact of Age and Motor Function in a Phase 1/2A Study of Infants with SMA Type 1 Receiving Single-Dose Gene Replacement Therapy. Pediatr Neurol. 2019 September; 98:39-45.

[11] Lenardo M J, Baltimore D. NF-κB: A pleiotropic mediator of inducible and tissue-specific gene control[J]. Cell, 1989, 58(2):227-229.

[12] Aloe L, Rocco M L, Bianchi P, et al. Nerve growth factor: from the early discoveries to the potential clinical use[J]. Journal of Translational Medicine, 2012, 10(1).

```
                            SEQUENCE LISTING

<160> NUMBER OF SEQ ID NOS: 16

<210> SEQ ID NO 1
<211> LENGTH: 2376
<212> TYPE: DNA
<213> ORGANISM: Artificial sequence
<220> FEATURE:
<223> OTHER INFORMATION: synthesized polynucleotide
<220> FEATURE:
<223> OTHER INFORMATION: Nucleic acid sequence of natural plasminogen
      (Glu-PLG, Glu-plasminogen) without signal peptide

<400> SEQUENCE: 1
gagcctctgg atgactatgt gaatacccag ggggcttcac tgttcagtgt cactaagaag        60
cagctgggag caggaagtat agaagaatgt gcagcaaaat gtgaggagga cgaagaattc       120
acctgcaggg cattccaata tcacagtaaa gagcaacaat gtgtgataat ggctgaaaac       180
aggaagtcct ccataatcat taggatgaga gatgtagttt tatttgaaaa gaaagtgtat       240
ctctcagagt gcaagactgg gaatggaaag aactacagag gacgatgtc caaaacaaaa        300 aatggcatca cctgtcaaaa atggagttcc acttctcccc acagacctag attctcacct       360
gctacacacc cctcagaggg actggaggag aactactgca ggaatccaga caacgatccg       420 cagggccct ggtgctatac tactgatcca gaaaagagat atgactactg cgacattctt        480
gagtgtgaag aggaatgtat gcattgcagt ggagaaaact atgacggcaa aatttccaag       540
accatgtctg gactggaatg ccaggcctgg gactctcaga gcccacacgc tcatggatac       600
attccttcca aatttccaaa caagaacctg aagaagaatt actgtcgtaa ccccgatagg       660
gagctgcggc cttggtgttt caccaccgac cccaacaagc gctgggaact ttgtgacatc       720
ccccgctgca caacacctcc accatcttct ggtcccacct accagtgtct gaagggaaca       780
ggtgaaaact atcgcgggaa tgtggctgtt accgtgtccg ggcacacctg tcagcactgg       840
agtgcacaga cccctcacac acataacagg acaccagaaa acttcccctg caaaaatttg       900
gatgaaaact actgccgcaa tcctgacgga aaaagggccc catggtgcca tacaaccaac       960
agccaagtgc ggtgggagta ctgtaagata ccgtcctgtg actcctcccc agtatccacg      1020
gaacaattgg ctcccacagc accacctgag ctaacccctg tggtccagga ctgctaccat      1080
ggtgatggac agagctaccg aggcacatcc tccaccacca ccacaggaaa gaagtgtcag      1140
tcttggtcat ctatgacacc acaccggcac cagaagaccc cagaaaacta cccaaatgct      1200
ggcctgacaa tgaactactg caggaatcca gatgccgata aaggcccctg tgtttttacc      1260 acagaccccca gcgtcaggtg ggagtactgc aacctgaaaa aatgctcagg aacagaagcg      1320
agtgttgtag cacctccgcc tgttgtcctg cttccagatg tagagactcc ttccgaagaa      1380
gactgtatgt ttgggaatgg gaaaggatac cgaggcaaga gggcgaccac tgttactggg      1440
acgccatgcc aggactgggc tgcccaggag ccccatagac acagcatttt cactccagag      1500
acaaatccac gggcgggtct ggaaaaaaat tactgccgta accctgatgg tgatgtaggt      1560
ggtccctggt gctacacgac aaatccaaga aaactttacg actactgtga tgtccctcag      1620
tgtgcggccc cttcatttga ttgtgggaag cctcaagtgg agccgaagaa atgtcctgga      1680
agggttgtag gggggtgtgt ggcccacca cattcctggc cctggcaagt cagtcttaga      1740
acaaggtttg gaatgcactt ctgtggaggc accttgatat ccccagagtg ggtgttgact      1800
```

-continued

```
gctgcccact gcttggagaa gtccccaagg ccttcatcct acaaggtcat cctgggtgca    1860
caccaagaag tgaatctcga accgcatgtt caggaaatag aagtgtctag gctgttcttg    1920
gagcccacac gaaaagatat tgccttgcta aagctaagca gtcctgccgt catcactgac    1980
aaagtaatcc cagcttgtct gccatcccca aattatgtgg tcgctgaccg gaccgaatgt    2040
ttcatcactg gctggggaga aacccaaggt acttttggag ctggccttct caaggaagcc    2100
cagctccctg tgattgagaa taaagtgtgc aatcgctatg agtttctgaa tggaagagtc    2160
caatccaccg aactctgtgc tgggcatttg gccggaggca ctgacagttg ccagggtgac    2220
agtggaggtc ctctggtttg cttcgagaag gacaaataca ttttacaagg agtcacttct    2280
tggggtcttg gctgtgcacg ccccaataag cctggtgtct atgttcgtgt ttcaaggttt    2340
gttacttgga ttgagggagt gatgagaaat aattaa                              2376
```

<210> SEQ ID NO 2
<211> LENGTH: 791
<212> TYPE: PRT
<213> ORGANISM: Artificial sequence
<220> FEATURE:
<223> OTHER INFORMATION: synthesized polypeptide
<220> FEATURE:
<223> OTHER INFORMATION: Amino acid sequence of natural plasminogen
      (Glu-PLG, Glu-plasminogen) without signal peptide

<400> SEQUENCE: 2

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
        195                 200                 205

Asn Leu Lys Lys Asn Tyr Cys Arg Asn Pro Asp Arg Glu Leu Arg Pro
    210                 215                 220

Trp Cys Phe Thr Thr Asp Pro Asn Lys Arg Trp Glu Leu Cys Asp Ile
225                 230                 235                 240
```

-continued

```
Pro Arg Cys Thr Thr Pro Pro Pro Ser Ser Gly Pro Thr Tyr Gln Cys
            245             250             255

Leu Lys Gly Thr Gly Glu Asn Tyr Arg Gly Asn Val Ala Val Thr Val
            260             265             270

Ser Gly His Thr Cys Gln His Trp Ser Ala Gln Thr Pro His Thr His
            275             280             285

Asn Arg Thr Pro Glu Asn Phe Pro Cys Lys Asn Leu Asp Glu Asn Tyr
    290             295             300

Cys Arg Asn Pro Asp Gly Lys Arg Ala Pro Trp Cys His Thr Thr Asn
305             310             315             320

Ser Gln Val Arg Trp Glu Tyr Cys Lys Ile Pro Ser Cys Asp Ser Ser
            325             330             335

Pro Val Ser Thr Glu Gln Leu Ala Pro Thr Ala Pro Pro Glu Leu Thr
            340             345             350

Pro Val Val Gln Asp Cys Tyr His Gly Asp Gly Gln Ser Tyr Arg Gly
            355             360             365

Thr Ser Ser Thr Thr Thr Thr Gly Lys Lys Cys Gln Ser Trp Ser Ser
    370             375             380

Met Thr Pro His Arg His Gln Lys Thr Pro Glu Asn Tyr Pro Asn Ala
385             390             395             400

Gly Leu Thr Met Asn Tyr Cys Arg Asn Pro Asp Ala Asp Lys Gly Pro
            405             410             415

Trp Cys Phe Thr Thr Asp Pro Ser Val Arg Trp Glu Tyr Cys Asn Leu
            420             425             430

Lys Lys Cys Ser Gly Thr Glu Ala Ser Val Val Ala Pro Pro Pro Val
            435             440             445

Val Leu Leu Pro Asp Val Glu Thr Pro Ser Glu Glu Asp Cys Met Phe
    450             455             460

Gly Asn Gly Lys Gly Tyr Arg Gly Lys Arg Ala Thr Thr Val Thr Gly
465             470             475             480

Thr Pro Cys Gln Asp Trp Ala Ala Gln Glu Pro His Arg His Ser Ile
            485             490             495

Phe Thr Pro Glu Thr Asn Pro Arg Ala Gly Leu Glu Lys Asn Tyr Cys
            500             505             510

Arg Asn Pro Asp Gly Asp Val Gly Gly Pro Trp Cys Tyr Thr Thr Asn
    515             520             525

Pro Arg Lys Leu Tyr Asp Tyr Cys Asp Val Pro Gln Cys Ala Ala Pro
    530             535             540

Ser Phe Asp Cys Gly Lys Pro Gln Val Glu Pro Lys Lys Cys Pro Gly
545             550             555             560

Arg Val Val Gly Gly Cys Val Ala His Pro His Ser Trp Pro Trp Gln
            565             570             575

Val Ser Leu Arg Thr Arg Phe Gly Met His Phe Cys Gly Gly Thr Leu
            580             585             590

Ile Ser Pro Glu Trp Val Leu Thr Ala Ala His Cys Leu Glu Lys Ser
            595             600             605

Pro Arg Pro Ser Ser Tyr Lys Val Ile Leu Gly Ala His Gln Glu Val
    610             615             620

Asn Leu Glu Pro His Val Gln Glu Ile Glu Val Ser Arg Leu Phe Leu
625             630             635             640

Glu Pro Thr Arg Lys Asp Ile Ala Leu Leu Lys Leu Ser Ser Pro Ala
            645             650             655

Val Ile Thr Asp Lys Val Ile Pro Ala Cys Leu Pro Ser Pro Asn Tyr
```

-continued

```
                   660              665              670

Val Val Ala Asp Arg Thr Glu Cys Phe Ile Thr Gly Trp Gly Glu Thr
            675              680              685

Gln Gly Thr Phe Gly Ala Gly Leu Leu Lys Glu Ala Gln Leu Pro Val
        690              695              700

Ile Glu Asn Lys Val Cys Asn Arg Tyr Glu Phe Leu Asn Gly Arg Val
705              710              715              720

Gln Ser Thr Glu Leu Cys Ala Gly His Leu Ala Gly Gly Thr Asp Ser
                725              730              735

Cys Gln Gly Asp Ser Gly Gly Pro Leu Val Cys Phe Glu Lys Asp Lys
            740              745              750

Tyr Ile Leu Gln Gly Val Thr Ser Trp Gly Leu Gly Cys Ala Arg Pro
        755              760              765

Asn Lys Pro Gly Val Tyr Val Arg Val Ser Arg Phe Val Thr Trp Ile
    770              775              780

Glu Gly Val Met Arg Asn Asn
785              790
```

```
<210> SEQ ID NO 3
<211> LENGTH: 2433
<212> TYPE: DNA
<213> ORGANISM: Artificial sequence
<220> FEATURE:
<223> OTHER INFORMATION: synthesized polynucleotide
<220> FEATURE:
<223> OTHER INFORMATION: Nucleic acid sequence of natural plasminogen
      (from swiss prot) with signal peptide

<400> SEQUENCE: 3
atggaacata aggaagtggt tcttctactt cttttatttc tgaaatcagg tcaaggagag      60
cctctggatg actatgtgaa tacccagggg gcttcactgt tcagtgtcac taagaagcag     120
ctgggagcag gaagtataga agaatgtgca gcaaaatgtg aggaggacga agaattcacc     180
tgcagggcat tccaatatca cagtaaagag caacaatgtg tgataatggc tgaaaacagg     240
aagtcctcca taatcattag gatgagagat gtagtttttat ttgaaaagaa agtgtatctc     300
tcagagtgca agactgggaa tggaaagaac tacagaggga cgatgtccaa aacaaaaaat     360
ggcatcacct gtcaaaaatg gagttccact tctccccaca gacctagatt ctcacctgct     420
acacacccct cagagggact ggaggagaac tactgcagga tccagacaa cgatccgcag      480 gggccctggt gctatactac tgatccagaa aagagatatg actactgcga cattcttgag     540
tgtgaagagg aatgtatgca ttgcagtgga aaaactatg acggcaaaat ttccaagacc      600
atgtctggac tggaatgcca ggcctgggac tctcagagcc cacacgctca tggatacatt     660
ccttccaaat ttccaaacaa gaacctgaag aagaattact gtcgtaaccc cgataggag       720 ctgcggcctt ggtgtttcac caccgacccc aacaagcgct gggaactttg tgacatcccc     780
cgctgcacaa cacctccacc atcttctggt cccacctacc agtgtctgaa gggaacaggt     840
gaaaactatc gcgggaatgt ggctgttacc gtgtccgggc acacctgtca gcactggagt     900
gcacagaccc ctcacacaca taacaggaca ccagaaaact ccccctgcaa aaatttggat     960
gaaaactact gccgcaatcc tgacggaaaa agggcccat ggtgccatac aaccaacagc     1020
caagtgcggt gggagtactg taagatacg tcctgtgact cctccccagt atccacggaa     1080
caattggctc ccacagcacc acctgagcta acccctgtgg tccaggactg ctaccatggt    1140
gatggacaga gctaccgagg cacatcctcc accaccacca caggaaagaa gtgtcagtct   1200
```

```
tggtcatcta tgacaccaca ccggcaccag aagaccccag aaaactaccc aaatgctggc      1260
ctgacaatga actactgcag gaatccagat gccgataaag gccctggtg ttttaccaca       1320 gaccccagcg tcaggtggga gtactgcaac ctgaaaaaat gctcaggaac agaagcgagt      1380
gttgtagcac ctccgcctgt tgtcctgctt ccagatgtag agactccttc cgaagaagac      1440
tgtatgtttg ggaatgggaa aggataccga ggcaagaggg cgaccactgt tactgggacg      1500
ccatgccagg actgggctgc ccaggagccc catagacaca gcattttcac tccagagaca      1560
aatccacggg cgggtctgga aaaaaattac tgccgtaacc ctgatggtga tgtaggtggt      1620
ccctggtgct acacgacaaa tccaagaaaa ctttacgact actgtgatgt ccctcagtgt      1680
gcggcccctt catttgattg tgggaagcct caagtggagc cgaagaaatg tcctggaagg      1740
gttgtagggg ggtgtgtggc ccacccacat tcctggccct ggcaagtcag tcttagaaca      1800
aggtttggaa tgcacttctg tggaggcacc ttgatatccc cagagtgggt gttgactgct      1860
gcccactgct tggagaagtc cccaaggcct tcatcctaca aggtcatcct gggtgcacac      1920
caagaagtga atctcgaacc gcatgttcag gaaatagaag tgtctaggct gttcttggag      1980
cccacacgaa aagatattgc cttgctaaag ctaagcagtc ctgccgtcat cactgacaaa      2040
gtaatcccag cttgtctgcc atccccaaat tatgtggtcg ctgaccggac cgaatgtttc      2100
atcactggct ggggagaaac ccaaggtact tttggagctg gccttctcaa ggaagcccag      2160
ctccctgtga ttgagaataa agtgtgcaat cgctatgagt ttctgaatgg aagagtccaa      2220
tccaccgaac tctgtgctgg gcatttggcc ggaggcactg acagttgcca gggtgacagt      2280
ggaggtcctc tggtttgctt cgagaaggac aaatacattt tacaaggagt cacttcttgg      2340
ggtcttggct gtgcacgccc caataagcct ggtgtctatg ttcgtgtttc aaggtttgtt      2400
acttggattg agggagtgat gagaaataat taa                                  2433
```

```
<210> SEQ ID NO 4
<211> LENGTH: 810
<212> TYPE: PRT
<213> ORGANISM: Artificial sequence
<220> FEATURE:
<223> OTHER INFORMATION: synthesized polypeptide
<220> FEATURE:
<223> OTHER INFORMATION: Amino acid sequence of natural plasminogen
      (from swiss prot) with signal peptide

<400> SEQUENCE: 4

Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125
```

-continued

```
Ser Thr Ser Pro His Arg Pro Arg Phe Ser Pro Ala Thr His Pro Ser
    130             135             140

Glu Gly Leu Glu Glu Asn Tyr Cys Arg Asn Pro Asp Asn Asp Pro Gln
145             150             155             160

Gly Pro Trp Cys Tyr Thr Thr Asp Pro Glu Lys Arg Tyr Asp Tyr Cys
            165             170             175

Asp Ile Leu Glu Cys Glu Glu Glu Cys Met His Cys Ser Gly Glu Asn
            180             185             190

Tyr Asp Gly Lys Ile Ser Lys Thr Met Ser Gly Leu Glu Cys Gln Ala
            195             200             205

Trp Asp Ser Gln Ser Pro His Ala His Gly Tyr Ile Pro Ser Lys Phe
    210             215             220

Pro Asn Lys Asn Leu Lys Lys Asn Tyr Cys Arg Asn Pro Asp Arg Glu
225             230             235             240

Leu Arg Pro Trp Cys Phe Thr Thr Asp Pro Asn Lys Arg Trp Glu Leu
            245             250             255

Cys Asp Ile Pro Arg Cys Thr Thr Pro Pro Pro Ser Ser Gly Pro Thr
            260             265             270

Tyr Gln Cys Leu Lys Gly Thr Gly Glu Asn Tyr Arg Gly Asn Val Ala
    275             280             285

Val Thr Val Ser Gly His Thr Cys Gln His Trp Ser Ala Gln Thr Pro
    290             295             300

His Thr His Asn Arg Thr Pro Glu Asn Phe Pro Cys Lys Asn Leu Asp
305             310             315             320

Glu Asn Tyr Cys Arg Asn Pro Asp Gly Lys Arg Ala Pro Trp Cys His
            325             330             335

Thr Thr Asn Ser Gln Val Arg Trp Glu Tyr Cys Lys Ile Pro Ser Cys
            340             345             350

Asp Ser Ser Pro Val Ser Thr Glu Gln Leu Ala Pro Thr Ala Pro Pro
            355             360             365

Glu Leu Thr Pro Val Val Gln Asp Cys Tyr His Gly Asp Gly Gln Ser
    370             375             380

Tyr Arg Gly Thr Ser Ser Thr Thr Thr Thr Gly Lys Lys Cys Gln Ser
385             390             395             400

Trp Ser Ser Met Thr Pro His Arg His Gln Lys Thr Pro Glu Asn Tyr
            405             410             415

Pro Asn Ala Gly Leu Thr Met Asn Tyr Cys Arg Asn Pro Asp Ala Asp
            420             425             430

Lys Gly Pro Trp Cys Phe Thr Thr Asp Pro Ser Val Arg Trp Glu Tyr
            435             440             445

Cys Asn Leu Lys Lys Cys Ser Gly Thr Glu Ala Ser Val Val Ala Pro
    450             455             460

Pro Pro Val Val Leu Leu Pro Asp Val Glu Thr Pro Ser Glu Glu Asp
465             470             475             480

Cys Met Phe Gly Asn Gly Lys Gly Tyr Arg Gly Lys Arg Ala Thr Thr
            485             490             495

Val Thr Gly Thr Pro Cys Gln Asp Trp Ala Ala Gln Glu Pro His Arg
            500             505             510

His Ser Ile Phe Thr Pro Glu Thr Asn Pro Arg Ala Gly Leu Glu Lys
            515             520             525

Asn Tyr Cys Arg Asn Pro Asp Gly Asp Val Gly Gly Pro Trp Cys Tyr
    530             535             540

Thr Thr Asn Pro Arg Lys Leu Tyr Asp Tyr Cys Asp Val Pro Gln Cys
```

```
545              550              555              560

Ala Ala Pro Ser Phe Asp Cys Gly Lys Pro Gln Val Glu Pro Lys Lys
            565              570              575

Cys Pro Gly Arg Val Val Gly Gly Cys Val Ala His Pro His Ser Trp
            580              585              590

Pro Trp Gln Val Ser Leu Arg Thr Arg Phe Gly Met His Phe Cys Gly
            595              600              605

Gly Thr Leu Ile Ser Pro Glu Trp Val Leu Thr Ala Ala His Cys Leu
    610              615              620

Glu Lys Ser Pro Arg Pro Ser Ser Tyr Lys Val Ile Leu Gly Ala His
625              630              635              640

Gln Glu Val Asn Leu Glu Pro His Val Gln Glu Ile Glu Val Ser Arg
            645              650              655

Leu Phe Leu Glu Pro Thr Arg Lys Asp Ile Ala Leu Leu Lys Leu Ser
            660              665              670

Ser Pro Ala Val Ile Thr Asp Lys Val Ile Pro Ala Cys Leu Pro Ser
            675              680              685

Pro Asn Tyr Val Val Ala Asp Arg Thr Glu Cys Phe Ile Thr Gly Trp
    690              695              700

Gly Glu Thr Gln Gly Thr Phe Gly Ala Gly Leu Leu Lys Glu Ala Gln
705              710              715              720

Leu Pro Val Ile Glu Asn Lys Val Cys Asn Arg Tyr Glu Phe Leu Asn
            725              730              735

Gly Arg Val Gln Ser Thr Glu Leu Cys Ala Gly His Leu Ala Gly Gly
            740              745              750

Thr Asp Ser Cys Gln Gly Asp Ser Gly Gly Pro Leu Val Cys Phe Glu
            755              760              765

Lys Asp Lys Tyr Ile Leu Gln Gly Val Thr Ser Trp Gly Leu Gly Cys
    770              775              780

Ala Arg Pro Asn Lys Pro Gly Val Tyr Val Arg Val Ser Arg Phe Val
785              790              795              800

Thr Trp Ile Glu Gly Val Met Arg Asn Asn
            805              810
```

```
<210> SEQ ID NO 5
<211> LENGTH: 2145
<212> TYPE: DNA
<213> ORGANISM: Artificial sequence
<220> FEATURE:
<223> OTHER INFORMATION: synthesized polynucleotide
<220> FEATURE:
<223> OTHER INFORMATION: Nucleic acid sequence of LYS77-PLG(Lys-
      plasminogen)

<400> SEQUENCE: 5
aaagtgtatc tctcagagtg caagactggg aatggaaaga actacagagg gacgatgtcc      60
aaaacaaaaa atggcatcac ctgtcaaaaa tggagttcca cttctcccca cagacctaga     120
ttctcacctg ctacacaccc ctcagaggga ctggaggaga actactgcag gaatccagac     180
aacgatccgc aggggccctg gtgctatact actgatccag aaaagagata tgactactgc     240
gacattcttg agtgtgaaga ggaatgtatg cattgcagtg agaaaacta tgacggcaaa      300 atttccaaga ccatgtctgg actggaatgc caggcctggg actctcagag cccacacgct     360
catggataca ttccttccaa atttccaaac aagaacctga agaagaatta ctgtcgtaac     420
cccgataggg agctgcggcc ttggtgtttc accaccgacc ccaacaagcg ctgggaactt     480
```

-continued

```
tgtgacatcc cccgctgcac aacacctcca ccatcttctg gtcccaccta ccagtgtctg      540
aagggaacag gtgaaaacta tcgcgggaat gtggctgtta ccgtgtccgg gcacacctgt      600
cagcactgga gtgcacagac ccctcacaca cataacagga caccagaaaa cttcccctgc      660
aaaaatttgg atgaaaacta ctgccgcaat cctgacggaa aaagggcccc atggtgccat      720
acaaccaaca gccaagtgcg gtgggagtac tgtaagatac cgtcctgtga ctcctcccca      780
gtatccacgg aacaattggc tcccacagca ccacctgagc taacccctgt ggtccaggac      840
tgctaccatg gtgatggaca gagctaccga ggcacatcct ccaccaccac cacaggaaag      900
aagtgtcagt cttggtcatc tatgacacca caccggcacc agaagacccc agaaaactac      960
ccaaatgctg gcctgacaat gaactactgc aggaatccag atgccgataa aggcccctgg     1020
tgttttacca cagaccccag cgtcaggtgg gagtactgca acctgaaaaa atgctcagga     1080
acagaagcga gtgttgtagc acctccgcct gttgtcctgc ttccagatgt agagactcct     1140
tccgaagaag actgtatgtt tgggaatggg aaaggatacc gaggcaagag ggcgaccact     1200
gttactggga cgccatgcca ggactgggct gcccaggagc cccatagaca cagcattttc     1260
actccagaga caaatccacg ggcgggtctg gaaaaaaatt actgccgtaa ccctgatggt     1320 gatgtaggt gtccctggtg ctacacgaca aatccaagaa aactttacga ctactgtgat     1380
gtccctcagt gtgcggcccc ttcatttgat tgtgggaagc ctcaagtgga gccgaagaaa     1440
tgtcctggaa gggttgtagg ggggtgtgtg gcccacccac attcctggcc ctggcaagtc     1500
agtcttagaa caaggtttgg aatgcacttc tgtggaggca ccttgatatc cccagagtgg     1560
gtgttgactg ctgcccactg cttggagaag tccccaaggc cttcatccta caaggtcatc     1620
ctgggtgcac accaagaagt gaatctcgaa ccgcatgttc aggaaataga agtgtctagg     1680
ctgttcttgg agcccacacg aaaagatatt gccttgctaa agctaagcag tcctgccgtc     1740
atcactgaca agtaatccc agcttgtctg ccatcccaa attatgtggt cgctgaccgg     1800
accgaatgtt tcatcactgg ctggggagaa acccaaggta cttttggagc tggccttctc     1860
aaggaagccc agctccctgt gattgagaat aaagtgtgca atcgctatga gtttctgaat     1920
ggaagagtcc aatccaccga actctgtgct gggcatttgg ccggaggcac tgacagttgc     1980
cagggtgaca gtggaggtcc tctggtttgc ttcgagaagg acaaatacat tttacaagga     2040
gtcacttctt ggggtcttgg ctgtgcacgc cccaataagc ctggtgtcta tgttcgtgtt     2100
tcaaggtttg ttacttggat tgagggagtg atgagaaata attaa                     2145
```

<210> SEQ ID NO 6
<211> LENGTH: 714
<212> TYPE: PRT
<213> ORGANISM: Artificial sequence
<220> FEATURE:
<223> OTHER INFORMATION: synthesized polypeptide
<220> FEATURE:
<223> OTHER INFORMATION: Amino acid sequence of LYS77-PLG(Lys-
     plasminogen)

<400> SEQUENCE: 6

```
Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
```

-continued

```
                50                      55                      60

Gly Pro Trp Cys Tyr Thr Thr Asp Pro Glu Lys Arg Tyr Asp Tyr Cys
65                  70                  75                  80

Asp Ile Leu Glu Cys Glu Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
            115                 120                 125

Pro Asn Lys Asn Leu Lys Lys Asn Tyr Cys Arg Asn Pro Asp Arg Glu
        130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
            195                 200                 205

His Thr His Asn Arg Thr Pro Glu Asn Phe Pro Cys Lys Asn Leu Asp
        210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
            275                 280                 285

Tyr Arg Gly Thr Ser Ser Thr Thr Thr Thr Gly Lys Lys Cys Gln Ser
        290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
                340                 345                 350

Cys Asn Leu Lys Lys Cys Ser Gly Thr Glu Ala Ser Val Val Ala Pro
            355                 360                 365

Pro Pro Val Val Leu Leu Pro Asp Val Glu Thr Pro Ser Glu Glu Asp
        370                 375                 380

Cys Met Phe Gly Asn Gly Lys Gly Tyr Arg Gly Lys Arg Ala Thr Thr
385                 390                 395                 400

Val Thr Gly Thr Pro Cys Gln Asp Trp Ala Ala Gln Glu Pro His Arg
                405                 410                 415

His Ser Ile Phe Thr Pro Glu Thr Asn Pro Arg Ala Gly Leu Glu Lys
                420                 425                 430

Asn Tyr Cys Arg Asn Pro Asp Gly Asp Val Gly Gly Pro Trp Cys Tyr
            435                 440                 445

Thr Thr Asn Pro Arg Lys Leu Tyr Asp Tyr Cys Asp Val Pro Gln Cys
        450                 455                 460

Ala Ala Pro Ser Phe Asp Cys Gly Lys Pro Gln Val Glu Pro Lys Lys
465                 470                 475                 480
```

-continued

```
Cys Pro Gly Arg Val Val Gly Gly Cys Val Ala His Pro His Ser Trp
            485             490             495

Pro Trp Gln Val Ser Leu Arg Thr Arg Phe Gly Met His Phe Cys Gly
            500             505             510

Gly Thr Leu Ile Ser Pro Glu Trp Val Leu Thr Ala Ala His Cys Leu
            515             520             525

Glu Lys Ser Pro Arg Pro Ser Ser Tyr Lys Val Ile Leu Gly Ala His
            530             535             540

Gln Glu Val Asn Leu Glu Pro His Val Gln Glu Ile Glu Val Ser Arg
545             550             555             560

Leu Phe Leu Glu Pro Thr Arg Lys Asp Ile Ala Leu Leu Lys Leu Ser
            565             570             575

Ser Pro Ala Val Ile Thr Asp Lys Val Ile Pro Ala Cys Leu Pro Ser
            580             585             590

Pro Asn Tyr Val Val Ala Asp Arg Thr Glu Cys Phe Ile Thr Gly Trp
            595             600             605

Gly Glu Thr Gln Gly Thr Phe Gly Ala Gly Leu Leu Lys Glu Ala Gln
            610             615             620

Leu Pro Val Ile Glu Asn Lys Val Cys Asn Arg Tyr Glu Phe Leu Asn
625             630             635             640

Gly Arg Val Gln Ser Thr Glu Leu Cys Ala Gly His Leu Ala Gly Gly
            645             650             655

Thr Asp Ser Cys Gln Gly Asp Ser Gly Gly Pro Leu Val Cys Phe Glu
            660             665             670

Lys Asp Lys Tyr Ile Leu Gln Gly Val Thr Ser Trp Gly Leu Gly Cys
            675             680             685

Ala Arg Pro Asn Lys Pro Gly Val Tyr Val Arg Val Ser Arg Phe Val
            690             695             700

Thr Trp Ile Glu Gly Val Met Arg Asn Asn
705             710
```

```
<210> SEQ ID NO 7
<211> LENGTH: 1245
<212> TYPE: DNA
<213> ORGANISM: Artificial sequence
<220> FEATURE:
<223> OTHER INFORMATION: synthesized polynucleotide
<220> FEATURE:
<223> OTHER INFORMATION: Nucleic acid sequence of delta-plg(delta-
      plasminogen)

<400> SEQUENCE: 7
gagcctctgg atgactatgt gaatacccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa gagcaacaat gtgtgataat ggctgaaaac     180
aggaagtcct ccataatcat taggatgaga gatgtagttt tatttgaaaa gaaagtgtat     240
ctctcagagt gcaagactgg gaatggaaag aactacagag ggacgatgtc caaaacaaaa     300
aatggcatca cctgtcaaaa atggagttcc acttctcccc acagacctag attctcacct     360
gctacacacc cctcagaggg actggaggag aactactgca ggaatccaga caacgatccg     420
cagggggcct ggtgctatac tactgatcca gaaaagagat atgactactg cgacattctt     480
gagtgtgaag aggcggcccc ttcatttgat tgtgggaagc ctcaagtgga gccgaagaaa     540
tgtcctggaa gggttgtagg ggggtgtgtg gcccacccac attcctggcc ctggcaagtc     600
```

-continued

```
agtcttagaa caaggtttgg aatgcacttc tgtggaggca ccttgatatc cccagagtgg    660
gtgttgactg ctgcccactg cttggagaag tccccaaggc cttcatccta caaggtcatc    720
ctgggtgcac accaagaagt gaatctcgaa ccgcatgttc aggaaataga agtgtctagg    780
ctgttcttgg agcccacacg aaaagatatt gccttgctaa agctaagcag tcctgccgtc    840
atcactgaca aagtaatccc agcttgtctg ccatccccaa attatgtggt cgctgaccgg    900
accgaatgtt tcatcactgg ctggggagaa acccaaggta cttttggagc tggccttctc    960
aaggaagccc agctccctgt gattgagaat aaagtgtgca atcgctatga gtttctgaat   1020
ggaagagtcc aatccaccga actctgtgct gggcatttgg ccggaggcac tgacagttgc   1080
cagggtgaca gtggaggtcc tctggtttgc ttcgagaagg acaaatacat tttacaagga   1140
gtcacttctt ggggtcttgg ctgtgcacgc cccaataagc ctggtgtcta tgttcgtgtt   1200
tcaaggtttg ttacttggat tgagggagtg atgagaaata attaa                   1245
```

```
<210> SEQ ID NO 8
<211> LENGTH: 414
<212> TYPE: PRT
<213> ORGANISM: Artificial sequence
<220> FEATURE:
<223> OTHER INFORMATION: synthesized polypeptide
<220> FEATURE:
<223> OTHER INFORMATION: Amino acid sequence of delta-plg(delta-
      plasminogen)

<400> SEQUENCE: 8

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Ala Ala Pro Ser Phe Asp Cys Gly Lys Pro Gln Val
                165                 170                 175

Glu Pro Lys Lys Cys Pro Gly Arg Val Val Gly Gly Cys Val Ala His
            180                 185                 190

Pro His Ser Trp Pro Trp Gln Val Ser Leu Arg Thr Arg Phe Gly Met
        195                 200                 205

His Phe Cys Gly Gly Thr Leu Ile Ser Pro Glu Trp Val Leu Thr Ala
    210                 215                 220

Ala His Cys Leu Glu Lys Ser Pro Arg Pro Ser Ser Tyr Lys Val Ile
225                 230                 235                 240
```

-continued

```
Leu Gly Ala His Gln Glu Val Asn Leu Glu Pro His Val Gln Glu Ile
            245                 250                 255

Glu Val Ser Arg Leu Phe Leu Glu Pro Thr Arg Lys Asp Ile Ala Leu
            260                 265                 270

Leu Lys Leu Ser Ser Pro Ala Val Ile Thr Asp Lys Val Ile Pro Ala
        275                 280                 285

Cys Leu Pro Ser Pro Asn Tyr Val Val Ala Asp Arg Thr Glu Cys Phe
    290                 295                 300

Ile Thr Gly Trp Gly Glu Thr Gln Gly Thr Phe Gly Ala Gly Leu Leu
305                 310                 315                 320

Lys Glu Ala Gln Leu Pro Val Ile Glu Asn Lys Val Cys Asn Arg Tyr
            325                 330                 335

Glu Phe Leu Asn Gly Arg Val Gln Ser Thr Glu Leu Cys Ala Gly His
            340                 345                 350

Leu Ala Gly Gly Thr Asp Ser Cys Gln Gly Asp Ser Gly Gly Pro Leu
        355                 360                 365

Val Cys Phe Glu Lys Asp Lys Tyr Ile Leu Gln Gly Val Thr Ser Trp
    370                 375                 380

Gly Leu Gly Cys Ala Arg Pro Asn Lys Pro Gly Val Tyr Val Arg Val
385                 390                 395                 400

Ser Arg Phe Val Thr Trp Ile Glu Gly Val Met Arg Asn Asn
            405                 410
```

```
<210> SEQ ID NO 9
<211> LENGTH: 1104
<212> TYPE: DNA
<213> ORGANISM: Artificial sequence
<220> FEATURE:
<223> OTHER INFORMATION: synthesized polynucleotide
<220> FEATURE:
<223> OTHER INFORMATION: Nucleic acid sequence of Mini-plg(small
      plasminogen)

<400> SEQUENCE: 9
gtcaggtggg agtactgcaa cctgaaaaaa tgctcaggaa cagaagcgag tgttgtagca      60
cctccgcctg ttgtcctgct tccagatgta gagactcctt ccgaagaaga ctgtatgttt     120
gggaatggga aaggataccg aggcaagagg gcgaccactg ttactgggac gccatgccag     180
gactgggctg cccaggagcc ccatagacac agcattttca ctccagagac aaatccacgg     240
gcgggtctgg aaaaaaatta ctgccgtaac cctgatggtg atgtaggtgg tccctggtgc     300
tacacgacaa atccaagaaa actttacgac tactgtgatg tccctcagtg tgcggcccct     360
tcatttgatt gtgggaagcc tcaagtggag ccgaagaaat gtcctggaag ggttgtaggg     420
gggtgtgtgg cccacccaca ttcctggccc tggcaagtca gtcttagaac aaggtttgga     480
atgcacttct gtggaggcac cttgatatcc ccagagtggg tgttgactgc tgcccactgc     540
ttggagaagt ccccaaggcc ttcatcctac aaggtcatcc tgggtgcaca ccaagaagtg     600
aatctcgaac cgcatgttca ggaaatagaa gtgtctaggc tgttcttgga gcccacacga     660
aaagatattg ccttgctaaa gctaagcagt cctgccgtca tcactgacaa agtaatccca     720
gcttgtctgc catccccaaa ttatgtggtc gctgaccgga ccgaatgttt catcactggc     780
tggggagaaa cccaaggtac ttttggagct ggccttctca aggaagccca gctccctgtg     840
attgagaata aagtgtgcaa tcgctatgag tttctgaatg gaagagtcca atccaccgaa     900
ctctgtgctg gcatttggc cggaggcact gacagttgcc aggtgacag tggaggtcct     960
```

-continued

```
ctggtttgct tcgagaagga caaatacatt ttacaaggag tcacttcttg gggtcttggc   1020
tgtgcacgcc ccaataagcc tggtgtctat gttcgtgttt caaggtttgt tacttggatt   1080
gagggagtga tgagaaataa ttaa                                          1104
```

<210> SEQ ID NO 10
<211> LENGTH: 367
<212> TYPE: PRT
<213> ORGANISM: Artificial sequence
<220> FEATURE:
<223> OTHER INFORMATION: synthesized polypeptide
<220> FEATURE:
<223> OTHER INFORMATION: Amino acid sequence of Mini-plg(small
      plasminogen)

<400> SEQUENCE: 10

```
Val Arg Trp Glu Tyr Cys Asn Leu Lys Lys Cys Ser Gly Thr Glu Ala
1               5                   10                  15

Ser Val Val Ala Pro Pro Val Val Leu Leu Pro Asp Val Glu Thr
            20                  25                  30

Pro Ser Glu Glu Asp Cys Met Phe Gly Asn Gly Lys Gly Tyr Arg Gly
        35                  40                  45

Lys Arg Ala Thr Thr Val Thr Gly Thr Pro Cys Gln Asp Trp Ala Ala
    50                  55                  60

Gln Glu Pro His Arg His Ser Ile Phe Thr Pro Glu Thr Asn Pro Arg
65                  70                  75                  80

Ala Gly Leu Glu Lys Asn Tyr Cys Arg Asn Pro Asp Gly Asp Val Gly
                85                  90                  95

Gly Pro Trp Cys Tyr Thr Thr Asn Pro Arg Lys Leu Tyr Asp Tyr Cys
                100                 105                 110

Asp Val Pro Gln Cys Ala Ala Pro Ser Phe Asp Cys Gly Lys Pro Gln
            115                 120                 125

Val Glu Pro Lys Lys Cys Pro Gly Arg Val Val Gly Gly Cys Val Ala
            130                 135                 140

His Pro His Ser Trp Pro Trp Gln Val Ser Leu Arg Thr Arg Phe Gly
145                 150                 155                 160

Met His Phe Cys Gly Gly Thr Leu Ile Ser Pro Glu Trp Val Leu Thr
                165                 170                 175

Ala Ala His Cys Leu Glu Lys Ser Pro Arg Pro Ser Ser Tyr Lys Val
                180                 185                 190

Ile Leu Gly Ala His Gln Glu Val Asn Leu Glu Pro His Val Gln Glu
            195                 200                 205

Ile Glu Val Ser Arg Leu Phe Leu Glu Pro Thr Arg Lys Asp Ile Ala
            210                 215                 220

Leu Leu Lys Leu Ser Ser Pro Ala Val Ile Thr Asp Lys Val Ile Pro
225                 230                 235                 240

Ala Cys Leu Pro Ser Pro Asn Tyr Val Val Ala Asp Arg Thr Glu Cys
                245                 250                 255

Phe Ile Thr Gly Trp Gly Glu Thr Gln Gly Thr Phe Gly Ala Gly Leu
                260                 265                 270

Leu Lys Glu Ala Gln Leu Pro Val Ile Glu Asn Lys Val Cys Asn Arg
            275                 280                 285

Tyr Glu Phe Leu Asn Gly Arg Val Gln Ser Thr Glu Leu Cys Ala Gly
        290                 295                 300

His Leu Ala Gly Gly Thr Asp Ser Cys Gln Gly Asp Ser Gly Gly Pro
305                 310                 315                 320
```

-continued

```
Leu Val Cys Phe Glu Lys Asp Lys Tyr Ile Leu Gln Gly Val Thr Ser
            325             330             335

Trp Gly Leu Gly Cys Ala Arg Pro Asn Lys Pro Gly Val Tyr Val Arg
        340             345             350

Val Ser Arg Phe Val Thr Trp Ile Glu Gly Val Met Arg Asn Asn
    355             360             365
```

```
<210> SEQ ID NO 11
<211> LENGTH: 750
<212> TYPE: DNA
<213> ORGANISM: Artificial sequence
<220> FEATURE:
<223> OTHER INFORMATION: synthesized polynucleotide
<220> FEATURE:
<223> OTHER INFORMATION: Nucleic acid sequence of Micro-plg(micro-
      plasminogen)

<400> SEQUENCE: 11
gccccttcat ttgattgtgg gaagcctcaa gtggagccga agaaatgtcc tggaagggtt      60
gtaggggggt gtgtggccca cccacattcc tggccctggc aagtcagtct tagaacaagg     120
tttggaatgc acttctgtgg aggcaccttg atatccccag agtgggtgtt gactgctgcc     180
cactgcttgg agaagtcccc aaggccttca tcctacaagg tcatcctggg tgcacaccaa     240
gaagtgaatc tcgaaccgca tgttcaggaa atagaagtgt ctaggctgtt cttggagccc     300
acacgaaaag atattgcctt gctaaagcta agcagtcctg ccgtcatcac tgacaaagta     360
atcccagctt gtctgccatc cccaaattat gtggtcgctg accggaccga atgtttcatc     420
actggctggg gagaaaccca aggtactttt ggagctggcc ttctcaagga gcccagctc      480 cctgtgattg agaataaagt gtgcaatcgc tatgagtttc tgaatggaag agtccaatcc     540
accgaactct gtgctgggca tttggccgga ggcactgaca gttgccaggg tgacagtgga     600
ggtcctctgg tttgcttcga agaggacaaa tacattttac aaggagtcac ttcttggggt     660
cttggctgtg cacgccccaa taagcctggt gtctatgttc gtgtttcaag gtttgttact     720
tggattgagg gagtgatgag aaataattaa                                      750
```

```
<210> SEQ ID NO 12
<211> LENGTH: 249
<212> TYPE: PRT
<213> ORGANISM: Artificial sequence
<220> FEATURE:
<223> OTHER INFORMATION: synthesized polypeptide
<220> FEATURE:
<223> OTHER INFORMATION: Amino acid sequence of Micro-plg(micro-
      plasminogen)

<400> SEQUENCE: 12

Ala Pro Ser Phe Asp Cys Gly Lys Pro Gln Val Glu Pro Lys Lys Cys
1               5               10              15

Pro Gly Arg Val Val Gly Gly Cys Val Ala His Pro His Ser Trp Pro
            20              25              30

Trp Gln Val Ser Leu Arg Thr Arg Phe Gly Met His Phe Cys Gly Gly
        35              40              45

Thr Leu Ile Ser Pro Glu Trp Val Leu Thr Ala Ala His Cys Leu Glu
    50              55              60

Lys Ser Pro Arg Pro Ser Ser Tyr Lys Val Ile Leu Gly Ala His Gln
65              70              75              80

Glu Val Asn Leu Glu Pro His Val Gln Glu Ile Glu Val Ser Arg Leu
            85              90              95
```

-continued

```
Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
                180                 185                 190

Asp Ser Cys Gln Gly Asp Ser Gly Gly Pro Leu Val Cys Phe Glu Lys
            195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245
```

<210> SEQ ID NO 13
<211> LENGTH: 684
<212> TYPE: DNA
<213> ORGANISM: Artificial sequence
<220> FEATURE:
<223> OTHER INFORMATION: synthesized polynucleotide
<220> FEATURE:
<223> OTHER INFORMATION: Nucleic acid sequence of serine protease domain

<400> SEQUENCE: 13

```
gttgtagggg ggtgtgtggc ccacccacat tcctggccct ggcaagtcag tcttagaaca      60
aggtttggaa tgcacttctg tggaggcacc ttgatatccc cagagtgggt gttgactgct     120
gcccactgct tggagaagtc cccaaggcct tcatcctaca aggtcatcct gggtgcacac     180
caagaagtga atctcgaacc gcatgttcag gaaatagaag tgtctaggct gttcttggag     240
cccacacgaa aagatattgc cttgctaaag ctaagcagtc ctgccgtcat cactgacaaa     300
gtaatcccag cttgtctgcc atccccaaat tatgtggtcg ctgaccggac cgaatgtttc     360
atcactggct ggggagaaac ccaaggtact tttggagctg gccttctcaa ggaagcccag     420
ctccctgtga ttgagaataa agtgtgcaat cgctatgagt ttctgaatgg aagagtccaa     480
tccaccgaac tctgtgctgg gcatttggcc ggaggcactg acagttgcca gggtgacagt     540
ggaggtcctc tggtttgctt cgagaaggac aaatacattt tacaaggagt cacttcttgg     600
ggtcttggct gtgcacgccc caataagcct ggtgtctatg ttcgtgtttc aaggtttgtt     660
acttggattg agggagtgat gaga                                            684
```

<210> SEQ ID NO 14
<211> LENGTH: 228
<212> TYPE: PRT
<213> ORGANISM: Artificial sequence
<220> FEATURE:
<223> OTHER INFORMATION: synthesized polypeptide
<220> FEATURE:
<223> OTHER INFORMATION: Amino acid sequence of serine protease domain

<400> SEQUENCE: 14

```
Val Val Gly Gly Cys Val Ala His Pro His Ser Trp Pro Trp Gln Val
```

-continued

```
1                5               10              15

Ser Leu Arg Thr Arg Phe Gly Met His Phe Cys Gly Gly Thr Leu Ile
            20              25              30

Ser Pro Glu Trp Val Leu Thr Ala Ala His Cys Leu Glu Lys Ser Pro
            35              40              45

Arg Pro Ser Ser Tyr Lys Val Ile Leu Gly Ala His Gln Glu Val Asn
            50              55              60

Leu Glu Pro His Val Gln Glu Ile Glu Val Ser Arg Leu Phe Leu Glu
65                      70              75                      80

Pro Thr Arg Lys Asp Ile Ala Leu Leu Lys Leu Ser Ser Pro Ala Val
                85              90              95

Ile Thr Asp Lys Val Ile Pro Ala Cys Leu Pro Ser Pro Asn Tyr Val
            100             105             110

Val Ala Asp Arg Thr Glu Cys Phe Ile Thr Gly Trp Gly Glu Thr Gln
            115             120             125

Gly Thr Phe Gly Ala Gly Leu Leu Lys Glu Ala Gln Leu Pro Val Ile
            130             135             140

Glu Asn Lys Val Cys Asn Arg Tyr Glu Phe Leu Asn Gly Arg Val Gln
145                     150             155                     160

Ser Thr Glu Leu Cys Ala Gly His Leu Ala Gly Gly Thr Asp Ser Cys
                165             170             175

Gln Gly Asp Ser Gly Gly Pro Leu Val Cys Phe Glu Lys Asp Lys Tyr
                180             185             190

Ile Leu Gln Gly Val Thr Ser Trp Gly Leu Gly Cys Ala Arg Pro Asn
            195             200             205

Lys Pro Gly Val Tyr Val Arg Val Ser Arg Phe Val Thr Trp Ile Glu
            210             215             220

Gly Val Met Arg
225
```

<210> SEQ ID NO 15
<211> LENGTH: 20
<212> TYPE: DNA
<213> ORGANISM: Artificial sequence
<220> FEATURE:
<223> OTHER INFORMATION: synthesized polynucleotide
<220> FEATURE:
<223> OTHER INFORMATION: Forward primer

<400> SEQUENCE: 15
gcggcggcag tggtggcggc                                                          20

<210> SEQ ID NO 16
<211> LENGTH: 22
<212> TYPE: DNA
<213> ORGANISM: Artificial sequence
<220> FEATURE:
<223> OTHER INFORMATION: synthesized polynucleotide
<220> FEATURE:
<223> OTHER INFORMATION: Reverse primer

<400> SEQUENCE: 16
agtagatcgg acagattttg ct                                                       22

The invention claimed is:

1. A method for treating spinal muscular atrophy (SMA) comprising administering a therapeutically effective amount of plasminogen to a subject suffering from SMA.

2. The method according to claim 1, wherein the plasminogen promotes transcription and/or expression of the survival motor neuron (SMN) gene.

3. The method according to claim 1, wherein the plasminogen improves muscle strength in the subject.

4. The method according to claim 1, wherein the plasminogen prolongs survival of the subject.

5. The method according to claim 1, wherein the plasminogen improves muscle tone in the subject.

6. The method according to claim 1, wherein the plasminogen promotes expression of NF-κB protein in the subject.

7. The method according to claim 1, wherein the plasminogen promotes growth and development in the subject.

8. The method according to claim 1, wherein the plasminogen is administered in combination with one or more other medicaments or therapies.

9. The method according to claim 1, wherein the plasminogen is administered by intravenous administration, intramuscular administration, intrathecal administration, nasal inhalation, aerosol inhalation, nasal drops, or eye drops.

10. The method according to claim 1, wherein the plasminogen comprises an amino acid sequence having at least 80%, 85%, 90%, 95%, 96%, 97%, 98% or 99% sequence identity with the amino acid sequence represented by SEQ ID NO: 2, 6, 8, 10 or 12, and has plasminogen activity.

11. The method according to claim 1, wherein the plasminogen is a protein comprising a plasminogen active fragment and having plasminogen activity.

12. The method according to claim 1, wherein the plasminogen is selected from the group consisting of: Glu-plasminogen, Lys-plasminogen, mini-plasminogen, micro-plasminogen, delta-plasminogen, or a variant thereof retaining plasminogen activity.

13. The method according to claim 1, wherein the plasminogen comprises an amino acid sequence represented by SEQ ID NO: 2, 6, 8, 10 or 12.

* * * * *